United States Patent
Jung et al.

(10) Patent No.: US 11,848,564 B2
(45) Date of Patent: Dec. 19, 2023

(54) CONVERTER DEVICE AND METHOD

(71) Applicant: Samsung Electronics Co., Ltd., Suwon-si (KR)

(72) Inventors: Seungchul Jung, Suwon-si (KR); Sang Joon Kim, Hwaseong-si (KR); Hankyu Lee, Suwon-si (KR); Hyungwoo Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 915 days.

(21) Appl. No.: 16/657,245

(22) Filed: Oct. 18, 2019

(65) Prior Publication Data

US 2020/0195036 A1 Jun. 18, 2020

(30) Foreign Application Priority Data

Dec. 12, 2018 (KR) .......................... 10-2018-0160219

(51) Int. Cl.
*H02M 3/04* (2006.01)
*H02J 50/10* (2016.01)
(Continued)

(52) U.S. Cl.
CPC .............. *H02J 50/10* (2016.02); *H02J 50/12* (2016.02); *H02M 3/04* (2013.01); *A61B 5/0538* (2013.01); *A61B 5/686* (2013.01)

(58) Field of Classification Search
CPC ........ H02J 50/12; H02J 2310/23; A61N 1/00; H02M 3/00; A61B 5/00
See application file for complete search history.

(56) References Cited

U.S. PATENT DOCUMENTS 8,531,165 B2 * 9/2013 Chen ..................... H02M 3/158
323/268
8,971,078 B2 * 3/2015 Lee ..................... H02M 7/4807
363/95
(Continued)

FOREIGN PATENT DOCUMENTS

WO WO 2018/136885 A1 7/2018

OTHER PUBLICATIONS

Extended European Search Report dated Apr. 29, 2020 in corresponding European Patent Application No. 19212847.8 (8 pages in English).
(Continued)

*Primary Examiner* — Rexford N Barnie
*Assistant Examiner* — Joseph N Inge
(74) *Attorney, Agent, or Firm* — NSIP Law

(57) ABSTRACT

A converter and a circuit device including the converter are disclosed. The converter includes an inductor including a first end and a second end, and a switching circuit connected to the inductor. The switching circuit includes a first switch to control a connection between the first end and a battery connected to the converter, a second switch to control a connection between the second end and a current output end configured to output a current generated through the inductor from the battery, a third switch to control a connection between the second end and a voltage output end configured to output a voltage generated from the battery, and a fourth switch to control a connection between the second end and a voltage input end configured to receive a voltage to charge the battery.

27 Claims, 17 Drawing Sheets

(51) Int. Cl.
*H02J 50/12* (2016.01)
*A61B 5/0538* (2021.01)
*A61B 5/00* (2006.01)

(56) References Cited

U.S. PATENT DOCUMENTS

| | | | |
|---|---|---|---|
| 10,396,681 B1* | 8/2019 | Bassi | H02M 7/483 |
| 2005/0264271 A1* | 12/2005 | Lam | H02M 1/10 323/282 |
| 2012/0235976 A1 | 9/2012 | Van Lier | |
| 2012/0274295 A1* | 11/2012 | Lin | H02M 3/1582 323/282 |
| 2014/0103728 A1 | 4/2014 | Shrivastava et al. | |
| 2014/0225577 A1* | 8/2014 | Ivanov | H02M 3/1582 323/225 |
| 2014/0246908 A1* | 9/2014 | Chew | H04Q 9/00 307/31 |
| 2015/0270709 A1 | 9/2015 | Abu Qahouq | |
| 2016/0099582 A1 | 4/2016 | Ramorini et al. | |
| 2017/0187187 A1 | 6/2017 | Amin et al. | |
| 2017/0271990 A1 | 9/2017 | Knoedgen et al. | |
| 2018/0169424 A1 | 6/2018 | Griffith et al. | |
| 2018/0280706 A1 | 10/2018 | Maile et al. | |
| 2019/0103766 A1* | 4/2019 | Von Novak, III | H02J 7/00712 |
| 2019/0305685 A1* | 10/2019 | Miki | H02M 3/1582 |
| 2020/0076298 A1 | 3/2020 | Jung et al. | |

OTHER PUBLICATIONS

Jiao et al., "A single-Inductor MIMO Buck-Boost Converter with Inductor-Peak-Current PFM Control for Multiple Energy Harvesting," ASICON 2017, IEEE, Oct. 25, 2017, pp. 706-709, XP033295024.

Amin et al., "MISIMO: A Multi-input Single-Inductor Multi-Output Energy Harvester Employing Event-Driven MPPT Control to Achieve 89% Peak Efficiency and a 60,000x Dynamic Range in 28nm FDSOI," ISSCC 2018, IEEE, 2018 IEEE International Solid-Stage Circuit Conference, Feb. 13, 2018, pp. 144-146, XP033328374.

Kim et al., "Single-Inductor Dual-Input Dual-Output Buck-Boost Fuel-Cell-Li-Ion Charging DC-DC Converter Supply," Digest of Technical Papers, 2009 IEEE International Solid-State Circuits Conference, Feb. 11, 2009, Georgia Institute of Technology, Atlanta, GA, U.S.A., 3 pages in English.

Chen et al., "Single Inductor, Multiple Input, Multiple Output (SIMIMO) Power Mixer-Charger-Supply System," Georgia Tech Analog, Power, and Energy IC Research Lab, Atlanta, GA, U.S.A., 6 pages in English.

Kim et al., "Dual-Source Single-Inductor 0.18-μm CMOS Charger-Supply with Nested Hysteretic and Adaptive On-Time PWM Control," Georgia Institute of Technology, Atlanta, GA U.S.A., 12 pages in English.

Yu et al., "A new multi-mode multi-input-multi-output (MIMO) converter in an efficient low-voltage energy harvesting system for a gas sensor," Microsystem Technologies, Springer, Jul. 13, 2018, 16 pages in English.

Van Dongen et al., "A Switched-Mode Multichannel Neural Stimulator with a Minimum Number of External Components," Biomedical Electronics Group, Delft University of Technology, The Netherlands, IEEE, 2013, pp. 1877-1880, 4 pages in English.

Amin et al., "MISIMO: A Multi-Input Single-Inductor Multi-Output Energy Harvester Employing Event-Driven MPPT Control to Achieve 89% Peak Efficiency and a 60,000$^x$ Dynamic Range in 28nm FDSOI," 2018 IEEE International Solid-State Circuits Conference, Feb. 13, 2018, University of California, San Diego, La Jolla, CA, U.S.A., 3 pages in English.

* cited by examiner

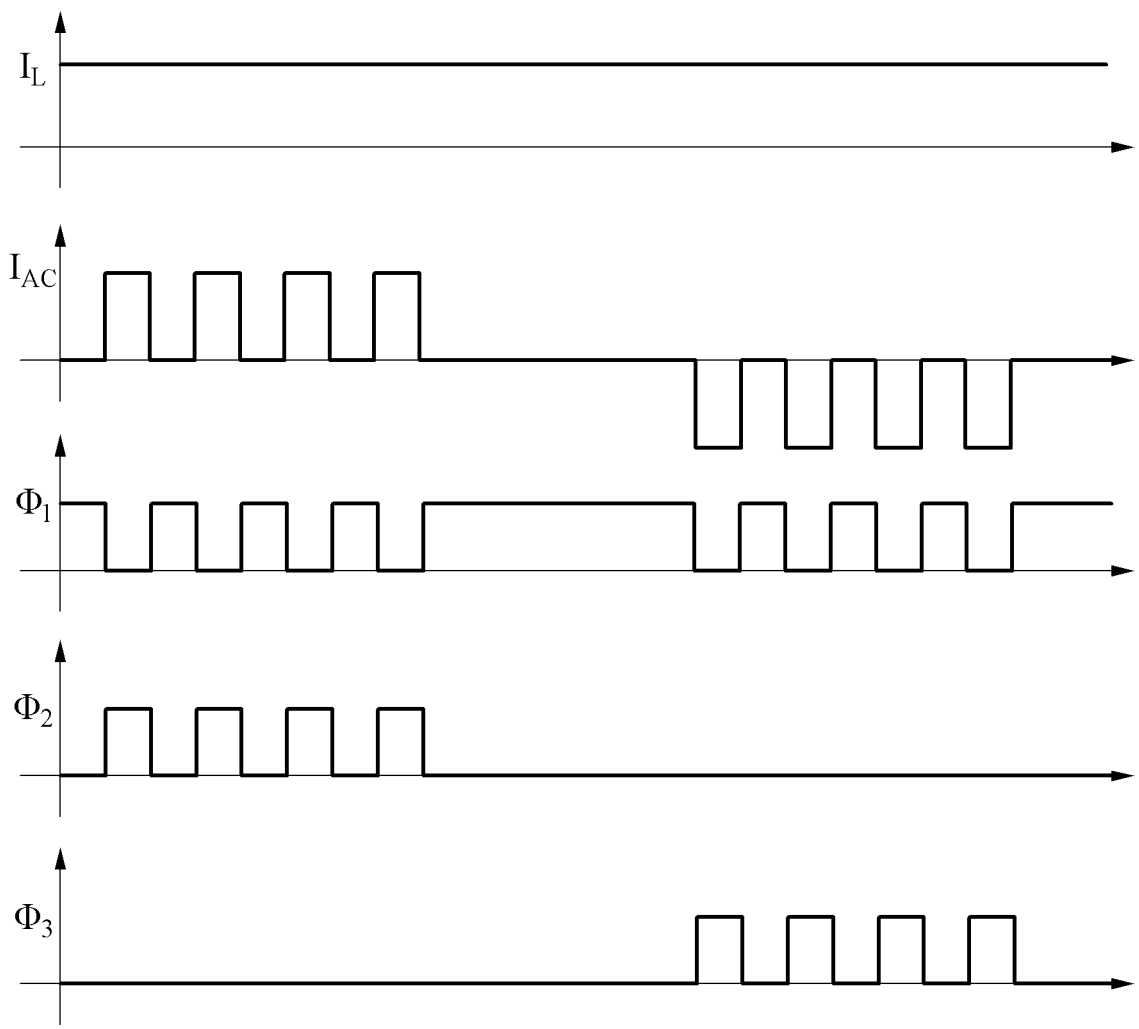

CONVERTER DEVICE AND METHOD

CROSS-REFERENCE TO RELATED APPLICATIONS

This application claims the benefit under 35 USC 119(a) of Korean Patent Application No. 10-2018-0160219 filed on Dec. 12, 2018, in the Korean Intellectual Property Office, the entire disclosure of which is incorporated herein by reference for all purposes.

BACKGROUND

1. Field

The following description relates to a converter device and method.

2. Description of Related Art

For ultra-compact devices, effective power conversion and minimization of external devices or elements may be needed. For effective power conversion, inductors may be needed. The inductors may be needed for multiple use purposes, for example, charging an internal battery in an ultra-compact device and outputting a voltage or a current from the internal battery. However, when providing a plurality of inductors in a single ultra-compact device to perform such multiple purposes, the size of the device may inevitably increase.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a converter includes an inductor having a first end and a second end, and a switching circuit connected to the inductor. The switching circuit includes a first switch configured to control a connection between the first end of the inductor and a battery connected to the converter, a second switch configured to control a connection between the second end of the inductor and a current output end outputting a current generated through the inductor from the battery, a third switch configured to control a connection between the second end of the inductor and a voltage output end outputting a voltage generated from the battery, and a fourth switch configured to control a connection between the second end of the inductor and a voltage input end receiving a voltage to charge the battery.

The switching circuit may further include a fifth switch configured to control a connection between the first end of the inductor and a ground; a sixth switch configured to control a connection between the second end of the inductor and the ground; and a seventh switch configured to control a connection between the second end of the inductor and the battery.

The switching circuit may further include a sixth switch configured to control a connection between the second end of the inductor and a ground, wherein the first switch may be configured to switch on during a timeslot in which the current may be output. The sixth switch may be configured to switch on during a first interval in the timeslot and off during a second interval in the timeslot, and the second switch may be configured to switch off during the first interval in the timeslot and on during the second interval in the timeslot.

The switching circuit may further include a fifth switch configured to control a connection between the first end of the inductor and a ground. The second switch may be configured to switch on during a timeslot in which the current may be output. The first switch may be configured to switch on during a first interval in the timeslot and off during a second interval in the timeslot. The fifth switch may be configured to switch off during the first interval in the timeslot and on during the second interval in the timeslot.

The switching circuit may further include a fifth switch configured to control a connection between the first end of the inductor and a ground and a sixth switch configured to control a connection between the second end of the inductor and the ground. The first switch and the sixth switch may be configured to switch on during a first interval in a timeslot in which the current may be output and off during a second interval in the timeslot. The second switch and the fifth switch may be configured to switch off during the first interval in the timeslot and on during the second interval in the timeslot.

The switching circuit may further include a fifth switch configured to control a connection between the first end of the inductor and a ground and a seventh switch configured to control a connection between the second end of the inductor and the battery. The fifth switch may be configured to switch on during a timeslot in which the current may be output. The seventh switch may be configured to switch on during a first interval in the timeslot and off during a second interval in the timeslot. The second switch may be configured to switch off during the first interval in the timeslot and on during the second interval in the timeslot.

The switching circuit may be configured to perform a switching operation on internal switches such that a first current may be output from the current output end during a first timeslot and a second current may be output, in a direction opposite to a direction of the first current, from the current output end during a second timeslot different from the first timeslot.

The switching circuit may further include a sixth switch configured to control a connection between the second end of the inductor and a ground. The first switch may be configured to switch on during a timeslot in which the voltage may be output. The sixth switch may be configured to switch on during a first interval in the timeslot and off during a second interval in the timeslot. The third switch may be configured to switch off during the first interval in the timeslot and on during the second interval in the timeslot.

The switching circuit may further include a fifth switch configured to control a connection between the first end of the inductor and a ground. The third switch may be configured to switch on during a timeslot in which the voltage may be output. The first switch may be configured to switch on during a first interval in the timeslot and off during a second interval in the timeslot. The fifth switch may be configured to switch off during the first interval in the timeslot and on during the second interval in the timeslot. The switching circuit may further include a fifth switch configured to control a connection between the first end of the inductor and a ground and, a sixth switch configured to control a connection between the second end of the inductor and the ground. The first switch and the sixth switch may be configured to switch on during a first interval in a timeslot in which the voltage may be output and off during a second interval in the timeslot. The third switch and the fifth switch may be configured to switch off during the first interval in the timeslot and on during the second interval in the timeslot.

The switching circuit may further include a fifth switch configured to control a connection between the first end of the inductor and a ground. The fourth switch may be configured to switch on during a timeslot in which the battery may be charged. The fifth switch may be configured to switch on during a first interval in the timeslot and off during a second interval in the timeslot. The first switch may be configured to switch off during the first interval in the timeslot and on during the second interval in the timeslot.

The switching circuit may be configured to perform one of a first switching operation to output the current generated through the inductor from the battery during one timeslot, a second switching operation to maintain the voltage generated from the battery to be constant, and a third switching operation to charge the battery.

The switching circuit may be configured to perform one switching operation selected from the first switching operation, the second switching operation, and the third switching operation, based on priorities of the first switching operation, the second switching operation, and the third switching operation.

Upon a determination to output a current from the current output end, the switching circuit may be configured to perform the first switching operation.

Upon a determination not to output a current from the current output end and the voltage output from the voltage output end may be determined insufficient, the switching circuit may be configured to perform the second switching operation.

Upon a determination charging of the battery may be possible, a determination not to output a current from the current output end, and the voltage output from the voltage output end may be determined sufficient, the switching circuit may be configured to perform the third switching operation.

Upon a determination not to output a current from the current output end and the voltage output from the voltage output end may be determined sufficient, and a determination charging the battery may be not possible, the switching circuit may be configured to skip the timeslot.

The switching circuit may further include a freewheeling switch configured to control a connection between the first end of the inductor and the second end of the inductor. The second switch may include an H-bridge connected to the second end of the inductor and configured to control a direction in which the current may be output to the current output end. The freewheeling switch may be configured to switch on during a first interval in a timeslot in which the current may be output and off during a second interval in the timeslot. A portion of switches of the H-bridge and a fifth switch may be configured to switch off during the first interval in the timeslot and on during the second interval in the timeslot. The portion of the switches of the H-bridge may be selected from the switches included in the H-bridge based on a direction in which the current may be output from the current output end.

The current to be output from the current output end may be in a form of pulse wave.

The inductor may be a single inductor.

The switching circuit may further include an eighth switch configured to control a connection between the second end of the inductor and a second voltage output end to which a second voltage generated from the battery may be output.

The converter may be configured to be inserted in a human body.

The voltage may be a constant voltage provided to one of a controller and a sensor that may be connected to the converter.

In another general aspect, a circuit device includes a battery, a power receiver, a converter, and a controller. The power receiver is configured to receive power to charge the battery. The converter is connected to the battery and the power receiver, comprising an inductor and a switching circuit. The controller is configured to control switching operations of the switching circuit to perform one of a first switching operation to output a current generated through the inductor from the battery, a second switching operation to maintain a voltage generated from the battery to be constant, and a third switching operation to charge the battery, using the inductor.

Other features and aspects will be apparent from the following detailed description, the drawings, and the claims.

BRIEF DESCRIPTION OF THE DRAWINGS

FIGS. 17 and 18 are diagrams illustrating examples of a switching operation to output a pulsed current using a freewheeling switch.

Figure 1:
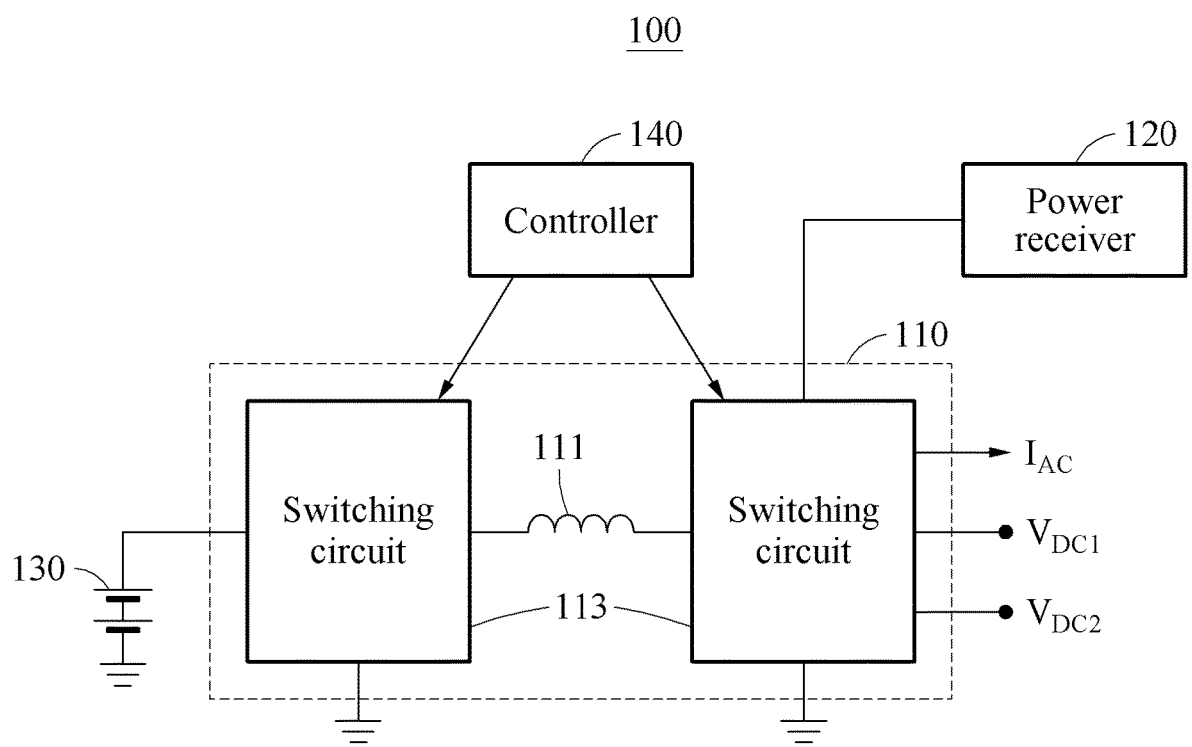
FIG. 1 is a diagram illustrating an example of a circuit device including a converter.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. As used herein, the term "and/or" includes any one and any combination of any two or more of the associated listed items.

Although terms such as "first," "second," and "third" may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

The terminology used herein is for describing various examples only and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein.

Also, in the description of example embodiments, detailed description of structures or functions that are thereby known after an understanding of the disclosure of the present application will be omitted when it is deemed that such description will cause ambiguous interpretation of the example embodiments.

Hereinafter, examples will be described in detail with reference to the accompanying drawings, and like reference numerals in the drawings refer to like elements throughout.

FIG. 1 is a diagram illustrating an example of a circuit device including a converter. Herein, a converter may also be referred to as a converter device while also noting that the converter device may also correspond to the circuit device in various examples.

Referring to FIG. 1, a circuit device 100 may include a converter 110, a power receiver 120, a battery 130, and a controller 140.

The converter 110 may include an inductor 111 and a switching circuit 113.

The inductor 111 is a single inductor included in the converter 110, and may be used when one of the switching operations to be performed by the switching circuit 113 to charge the battery 130, output a current, or maintain a voltage is performed. The maintaining of the voltage indicates a control operation performed to output a constant magnitude of voltage. The inductor 111 may be, for example, an external inductor. Herein, it is noted that use of the term 'may' with respect to an example or embodiment, e.g., as to what an example or embodiment may include or implement, means that at least one example or embodiment exists where such a feature is included or implemented while all examples and embodiments are not limited thereto.

The switching circuit 113 may include a plurality of switches and perform the switching operations by connecting at least two of the power receiver 120, the battery 130, voltage output ends, and current output ends. For example, the switching circuit 113 may perform one of a switching operation to charge the battery 130 based on power received by the power receiver 120, a switching operation to output a current $I_{AC}$ generated through the inductor 111 from the battery 130, and a switching operation to maintain voltages $V_{DC1}$ and $V_{DC2}$ generated from the battery 130 to be constant. The switching operations may be performed in different timeslots, and timeslot-based time division control will be further described in detail with reference to FIG. 13.

In this example, the current $I_{AC}$ may be an alternating current (AC) of a predefined waveform, and may be a stimulating current configured to be applied to living tissue or a current to be used for impedance measurement. The voltages $V_{DC1}$ and $V_{DC2}$ may be constant voltages. Although only a single current $I_{AC}$ and two voltages $V_{DC1}$ and $V_{DC2}$ are illustrated to be output in the example of FIG. 1 for convenience of description, examples are not limited to the illustrated example, and various numbers of currents and voltages may be output in various examples.

The switching operations described above may be performed based on the inductor 111. That is, examples include multiple purposes that may be achieved based on the inductor 111, which is a single inductor, for example, battery charging, current output, and voltage maintenance. Thus, by sharing such a single inductor as described above, it may be possible to minimize the number of internal inductor elements or devices used and reduce the size of the converter 110 accordingly. In addition, it may be possible to provide the converter 110 in which the current output and the voltage output are combined or mixed by using the single inductor.

The power receiver 120 receives power to charge the battery 130. For example, the power receiver 120 may receive power based on a wireless power transfer method, or receive power transferred through a power line.

The battery 130 may be charged by the power received by the power receiver 120, and may provide power to output a current or a voltage from the converter 110.

The controller 140 controls the switching operations of the switching circuit 113. For example, the controller 140 may control the switching operation to charge the battery 130, the switching operation to output the current generated from the converter 110, or the switching operation to maintain the voltage output from the converter 110 to be constant.

The circuit device 100 may include, for example, an implantable device, a wearable device, a stimulating device configured to output a stimulating current, and a current generator configured to output a current to be used for impedance measurement. The circuit device 100 may be applied to an extremely small bio-implantable system or an internet of things (IoT) system that requires a highly efficient and extremely small device or element. The circuit device 100 may be embodied in a form of chip and provided in, for example, a smartphone and an IoT device to which a voltage needs to be supplied.

Figure 2:
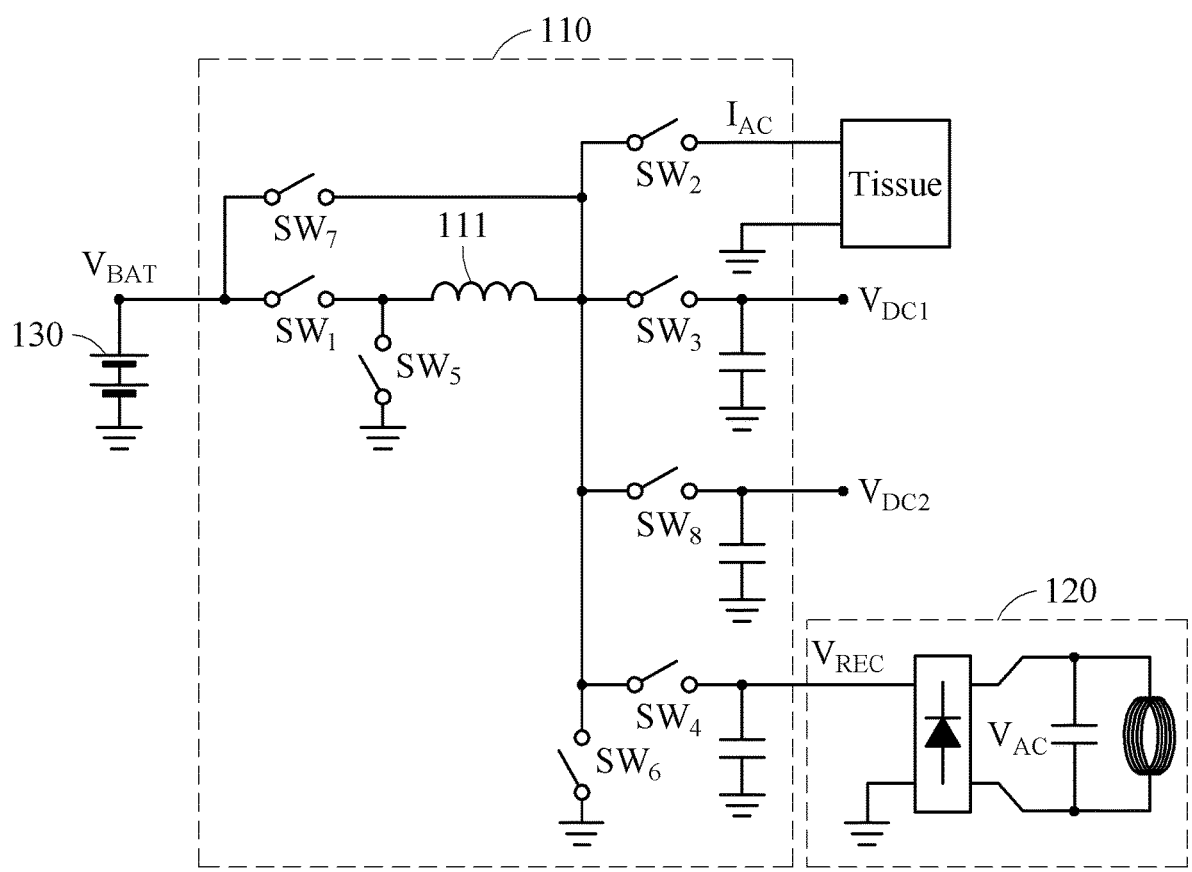
FIG. 2 is a circuit diagram illustrating an example of a circuit device including a converter.

FIG. 2 is a circuit diagram illustrating an example of a circuit device including a converter.

Referring to FIG. 2, a circuit device 100 may include a converter 110, a power receiver 120, a battery 130, and a controller. The controller is omitted from the example illustrated in FIG. 2 for convenience of description.

The converter 110 may include an inductor 111 and a plurality of switches, for example, a first switch $SW_1$ through an eighth switch $SW_8$ as illustrated.

The inductor 111 may include a first end and a second end. In the example illustrated in FIG. 2, a left end of the inductor 111 is referred to as the first end, and a right end of the inductor 111 is referred to as the second end. In this example, the inductor 111 is a single inductor included in the converter 110.

The first switch $SW_1$ controls a connection between the first end of the inductor 111 and the battery 130. The second switch $SW_2$ controls a connection between the second end of the inductor 111 and a current output end to which a current $I_{AC}$ is output. The current $I_{AC}$ is a current generated through the inductor 111 from the battery 130 and has a predefined waveform. The third switch $SW_3$ controls a connection between the second end of the inductor 111 and a first voltage output end to which a first voltage $V_{DC1}$ is output. The first voltage $V_{DC1}$ is the first constant voltage generated from the battery 130. The fourth switch $SW_4$ controls a connection between the second end of the inductor 111 and a voltage input end to which a voltage to be used to charge the battery 130 is input.

The fifth switch $SW_5$ controls a connection between the first end of the inductor 111 and a ground. The sixth switch $SW_6$ controls a connection between the second end of the inductor 111 and the ground. The seventh switch $SW_7$ controls a connection between the second end of the inductor 111 and the battery 130. The eighth switch $SW_8$ controls a connection between the second end of the inductor 111 and a second voltage output end to which a second voltage $V_{DC2}$ is output. The second voltage $V_{DC2}$ is a second constant voltage generated from the battery 130.

The power receiver 120 may include a coil and a rectifier. The power receiver 120 may receive power wirelessly transferred through the coil and convert an AC voltage received through the rectifier to a direct current (DC) rectifier voltage $V_{REC}$.

Although a current output from a current output end is illustrated and configured to be applied to a tissue in the example of FIG. 2 for convenience of description, examples are not limited to the illustrated example, and any examples related to applying a current output from the converter 110 may also be applicable without limitation.

Figure 3:
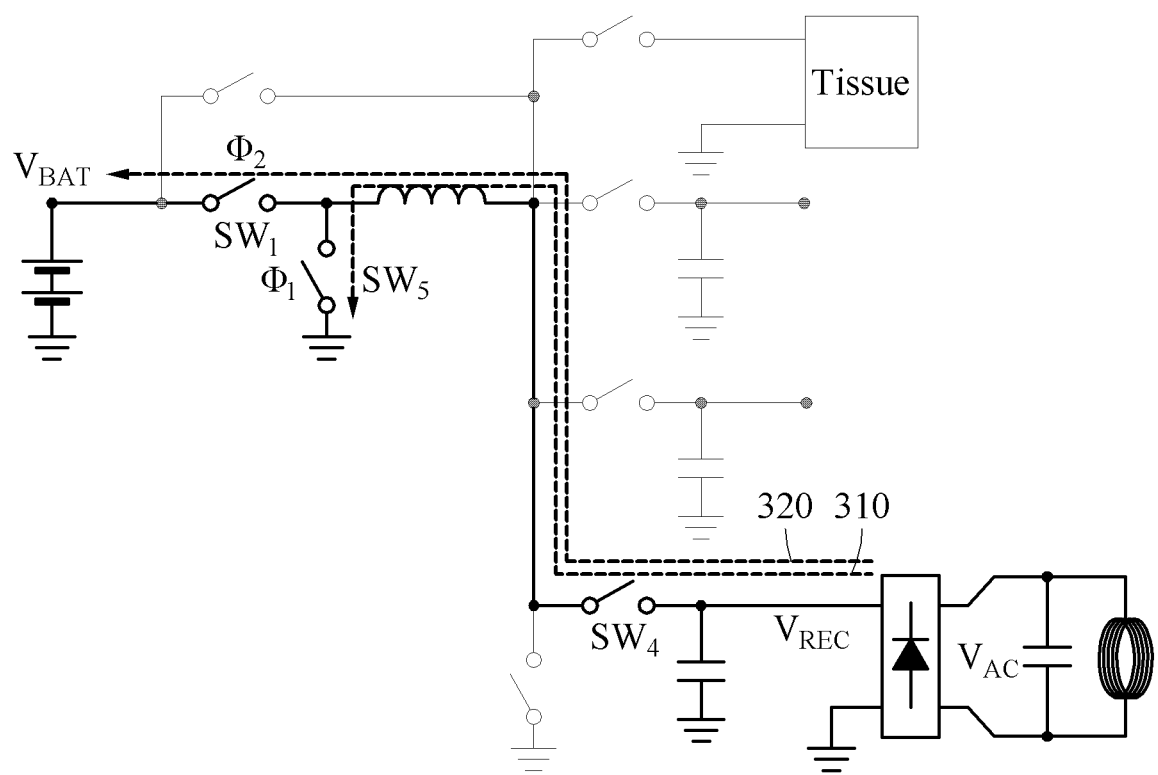
FIGS. 3 and 4 are diagrams illustrating examples of a switching operation to charge a battery.
Figure 4:
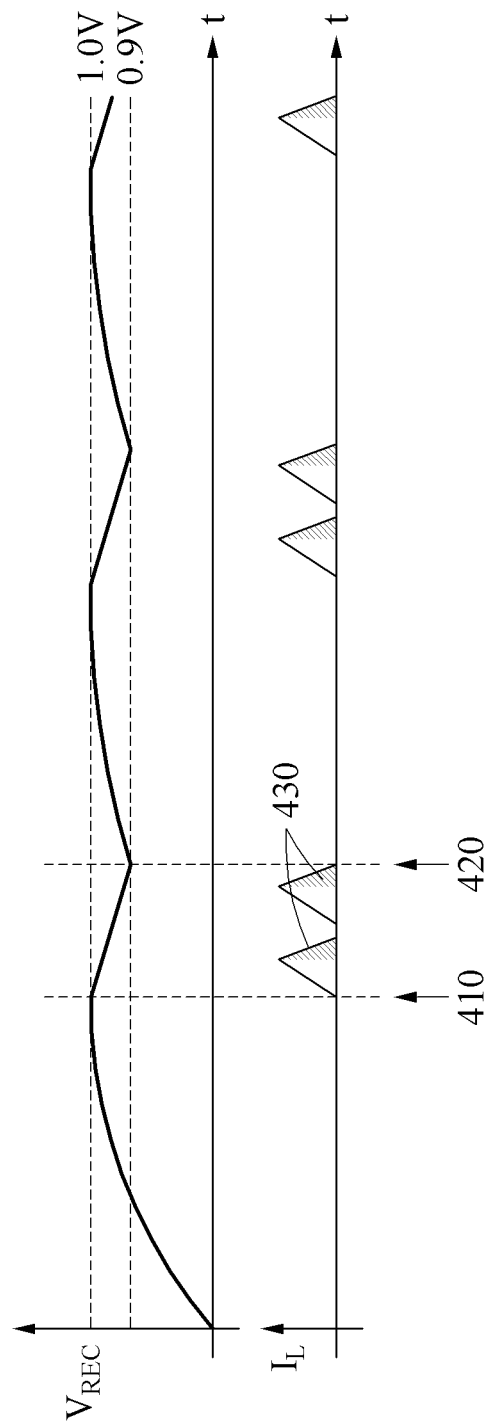

FIGS. 3 and 4 are diagrams illustrating examples of a switching operation to charge a battery.

A desirable voltage conversion may be desired to charge a battery with wirelessly received power. In general, a voltage received through a wireless power transfer method may be insufficient in its magnitude to charge a battery. Thus, a boost converter may be desired to boost the voltage to an adequate level. The boost converter may be performed using a single inductor for highly efficient charging. Hereinafter, a switching operation performed to charge a battery will be further described in detail with reference to FIG. 3.

Referring to FIG. 3, a switching operation corresponding to such a boost converter described above may be performed to charge a battery. This switching operation uses a first switch $SW_1$, a fourth switch $SW_4$, and a fifth switch $SW_5$, as illustrated, to charge the battery. The fourth switch $SW_4$ is configured and/or controlled to switch on during a timeslot in which the battery is charged. The fifth switch $SW_5$ is configured and/or controlled to switch on during a first interval in the timeslot and off during a second interval in the timeslot. The first switch $SW_1$ is off during the first interval in the timeslot and on during the second interval in the timeslot. Herein, that a switch is configured and/or controlled to switch on indicates that the switch is closed (for connection), and a switch is off when the switch is open (for disconnection). An inductor current may be reduced during the second interval in the timeslot, and the first switch $SW_1$ may be turned off even in the middle of the second interval when the inductor current reaches 0. That is, a current flow during the first interval in the timeslot in which the battery is charged is as indicated by a first arrow 310 and a current flow during the second interval in the timeslot in which the battery is charged is as indicated by a second arrow 320.

FIG. 4 illustrates a rectifier voltage $V_{REC}$ and an inductor current $I_L$ during a timeslot in which a battery is charged. The timeslot in which the battery is charged indicates a section between a first point 410 in time and a second point 420 in time.

When power is received by a power receiver, the rectifier voltage $V_{REC}$ may gradually increase. When the rectifier voltage $V_{REC}$ suffices to charge the battery, charging of the battery may then be initiated. For example, when the rectifier voltage $V_{REC}$ is greater than or equal to a first reference voltage, for example, 1.0 volts (V), the rectifier voltage $V_{REC}$ may be determined to suffice.

When the charging of the battery is initiated, the rectifier voltage $V_{REC}$ may gradually decrease, and energy may be stored in an inductor during a first interval in the timeslot, and thus the inductor current $I_L$ may gradually increase. The energy stored in the inductor may be transferred to the battery during a second interval in the timeslot, which may decrease the inductor current $I_L$ again and may require the charging of the battery by an electrical charge quantity 430. The charging of the battery may continue until the rectifier voltage $V_{REC}$ is insufficient to charge the battery or the timeslot ends. For example, when the rectifier voltage $V_{REC}$ decreases to be less than a second reference voltage, for example, 0.9V, the rectifier voltage $V_{REC}$ may be determined to be insufficient.

An output end of a converter that is configured to perform boost conversion when charging the battery may be connected to the battery to constantly fix an output voltage of the converter to always be the same upon fixing, in an example. Thus, an open-loop control that does not need rectification control for charging may be applied.

FIGS. 5 through 8 are diagrams illustrating examples of a switching operation to maintain a voltage.

Figure 5:
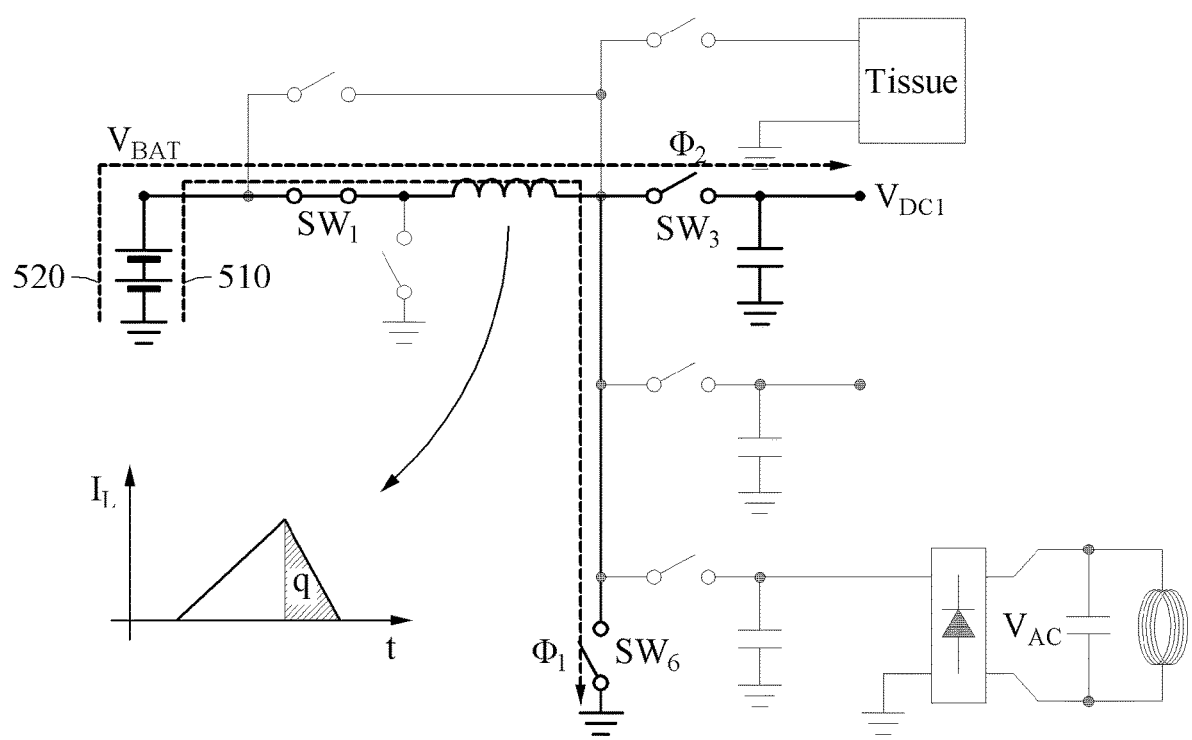
FIGS. 5 through 8 are diagrams illustrating examples of a switching operation to maintain a voltage.

A desirable DC-DC voltage converter may be desired to generate and output a voltage from a battery. Here, closed-loop control may be applied because rectification control is desired to constantly fix and regulate an output voltage. FIG. 5 illustrates an example of how a first voltage $V_{DC1}$ is output from a first voltage output end through a switching operation corresponding to the boost converter. In a case in which the first voltage $V_{DC1}$ needs to be maintained to be greater than a battery voltage $V_{BAT}$, the switching operation of the boost converter may be performed.

Referring to FIG. 5, for the switching operation performed to output the first voltage $V_{DC1}$, a first switch $SW_1$, a third switch $SW_3$, and a sixth switch $SW_6$ are used. The first switch $SW_1$ is configured and/or controlled to switch on during a timeslot in which the first voltage $V_{DC1}$ is output. The sixth switch $SW_6$ is configured and/or controlled to switch on during a first interval in the timeslot and off during a second interval in the timeslot. The third switch $SW_3$ is off during the first interval in the timeslot and on during the second interval in the timeslot. An inductor current may decrease during the second interval, and the third switch $SW_3$ may be turned off even in the middle of the second interval when the inductor current reaches 0. That is, a current flow during the first interval in the timeslot in which the first voltage $V_{DC1}$ is output is as indicated by a first arrow 510, and a current flow during the second interval in the timeslot in which the first voltage $V_{DC1}$ is output is as indicated by a second arrow 520. In this example, an inductor current $I_L$ increases in the first interval and decreases in the second interval, and energy is transferred to the first voltage output end by an electrical charge quantity q such that a voltage to be output from the first voltage output end reaches the first voltage $V_{DC1}$.

Figure 6:
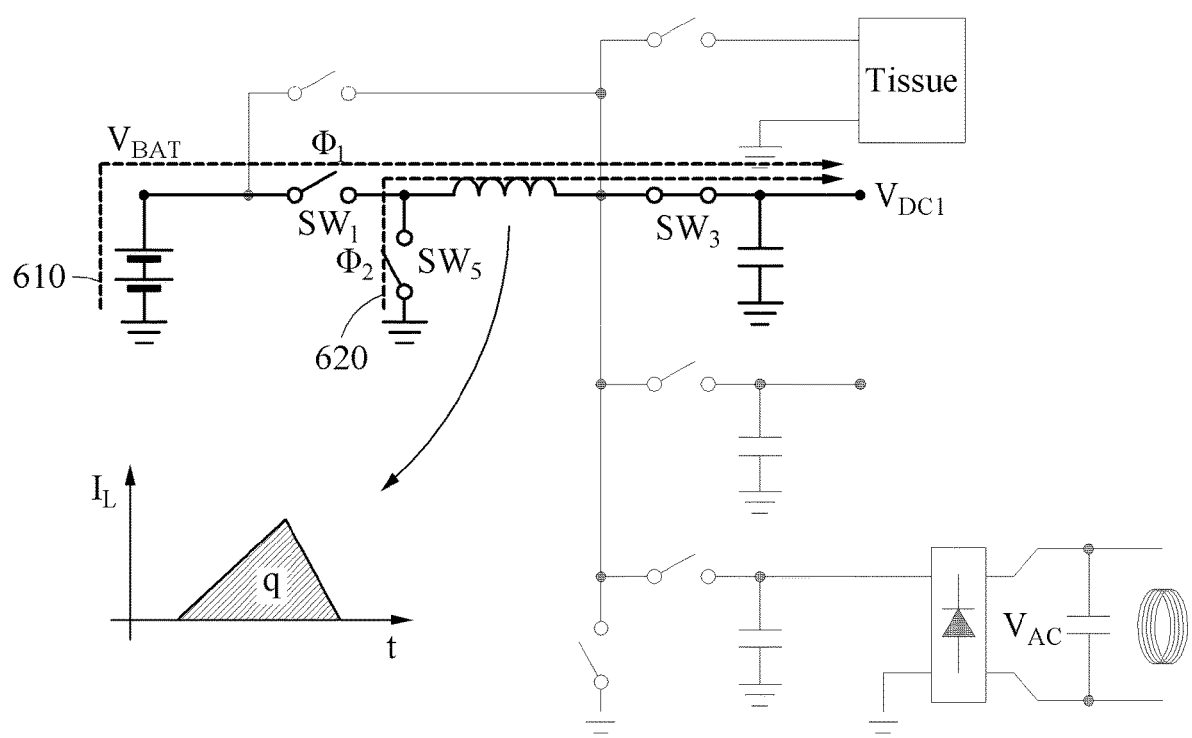

FIG. 6 illustrates an example of how a first voltage $V_{DC1}$ is output from a first voltage output end through a switching operation corresponding to operations of a buck converter. In a case in which the first voltage $V_{DC1}$ needs to be maintained to be less than a battery voltage $V_{BAT}$, the switching operation of the buck converter may be performed.

Referring to FIG. 6, for the switching operation performed to output the first voltage $V_{DC1}$, a first switch $SW_1$, a third switch $SW_3$, and a fifth switch $SW_5$ are used. The third switch $SW_3$ is configured and/or controlled to switch on during a timeslot in which the first voltage $V_{DC1}$ is output. The first switch $SW_1$ is configured and/or controlled to switch on during a first interval in the timeslot and off during a second interval in the timeslot. The fifth switch $SW_5$ is off during the first interval in the timeslot and on during the second interval in the timeslot. An inductor current may decrease during the second interval, and the fifth switch $SW_5$ may be turned off even in the middle of the second interval when the inductor current reaches 0. That is a current flow during the first interval in the timeslot in which the first voltage $V_{DC1}$ is output is as indicated by a first arrow 610 and a current flow during the second interval in the timeslot in which the first voltage $V_{DC1}$ is output is as indicated by a second arrow 620. In this example, an inductor current $I_L$ increases in the first interval and decreases in the second interval, and energy is transferred to the first voltage output end by an electrical charge quantity q such that a voltage to be output from the first voltage output end reaches the first voltage $V_{DC1}$.

Figure 7:
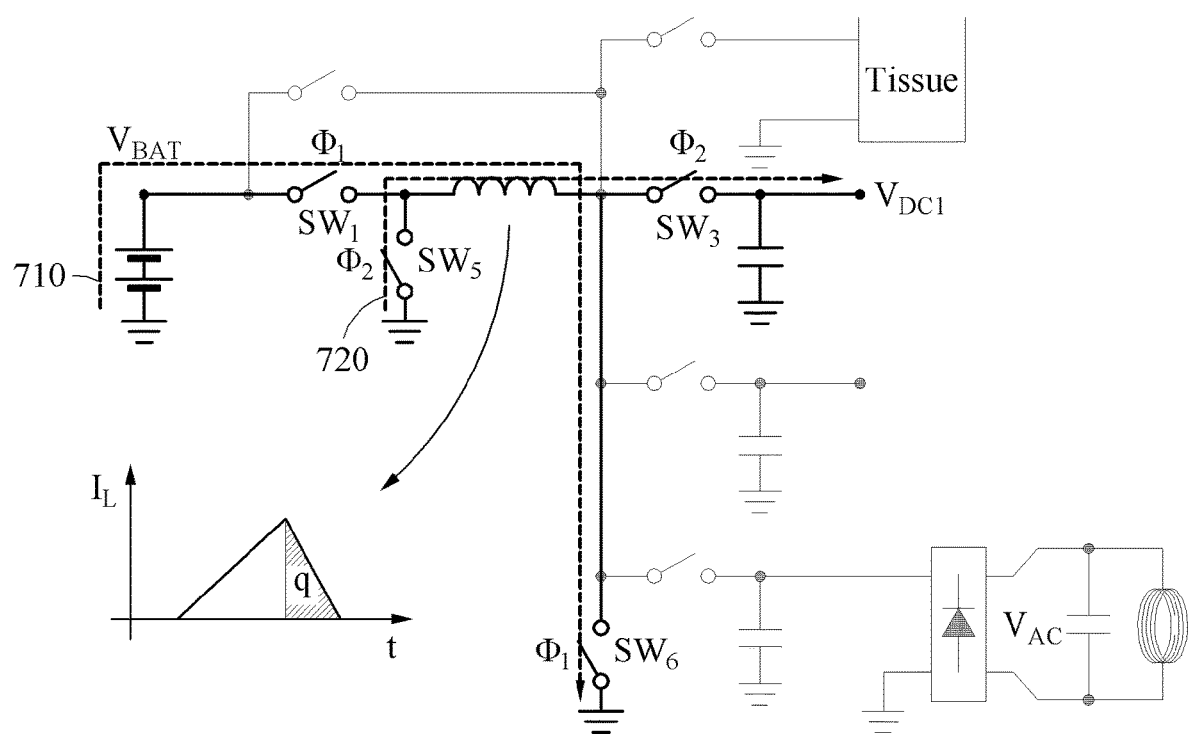

FIG. 7 illustrates an example of how a first voltage $V_{DC1}$ is output from a first voltage output end through a switching operation corresponding to operations of a buck-boost converter. In a case in which the first voltage $V_{DC1}$ needs to be maintained to be greater than, less than, or equal to a battery voltage $V_{BAT}$, the switching operation of the buck-boost converter may be performed.

Referring to FIG. 7, for the switching operation performed to output the first voltage $V_{DC1}$, a first switch $SW_1$, a third switch $SW_3$, a fifth switch $SW_5$, and a sixth switch $SW_6$ are used. The first switch $SW_1$ and the sixth switch $SW_6$ are on during the first interval in a timeslot in which the first voltage $V_{DC1}$ is output, and off during a second interval in the timeslot. The third switch $SW_3$ and the fifth switch $SW_5$ are off during the first interval in the timeslot and on during the second interval in the timeslot. An inductor current may decrease during the second interval, and the fifth switch $SW_5$ may be turned off when the inductor current reaches 0. In this example, an inductor current $I_L$ increases in the first interval and decreases in the second interval, and energy is transferred to the first voltage output end by an electrical charge quantity q such that a voltage to be output from the first voltage output end reaches the first voltage $V_{DC1}$.

Figure 8:
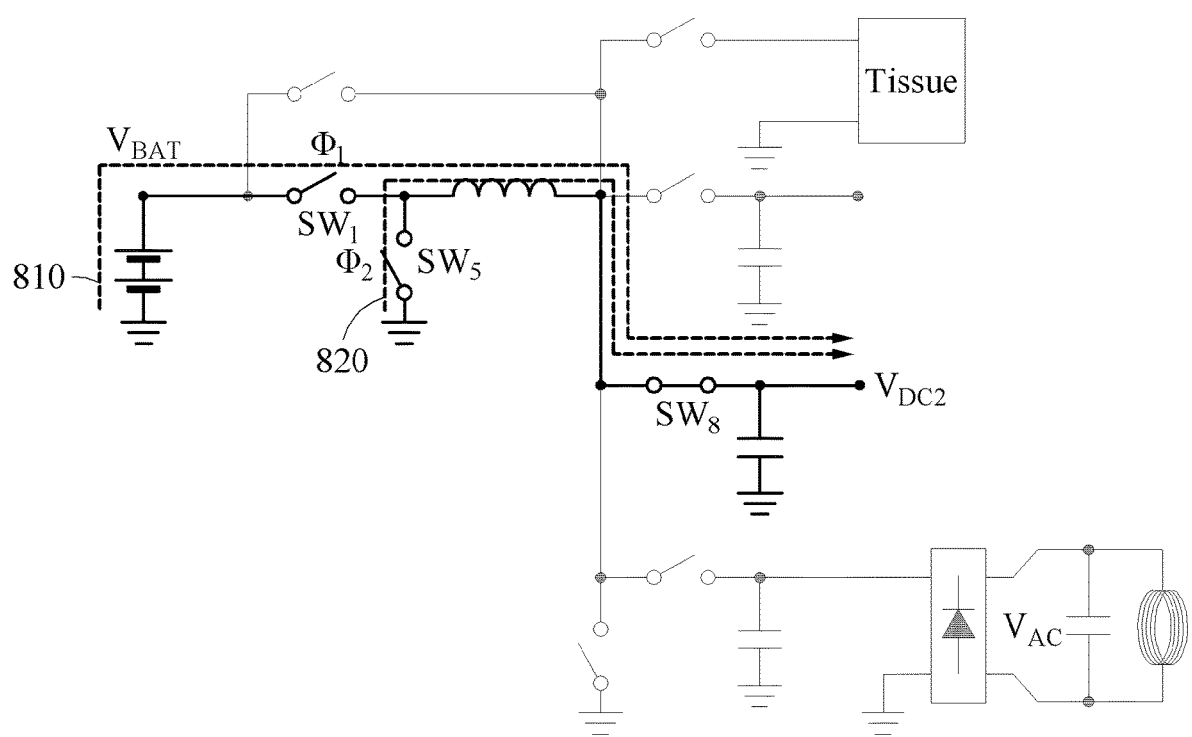

FIG. 8 illustrates an example of how a second voltage $V_{DC2}$ is output from a second voltage output end. Referring to FIG. 8, a switching operation performed to maintain the second voltage $V_{DC2}$ uses an eighth switch $SW_8$ connected to the second voltage output end in lieu of a third switch $SW_3$ connected to a first voltage output end. For example, in a case in which the second voltage $V_{DC2}$ is output through a switching operation of buck converter as illustrated in the example of FIG. 8, a first switch $SW_1$, a fifth switch $SW_5$, and the eighth switch $SW_8$ may be used. The eighth switch $SW_8$ is configured and/or controlled to switch on during a timeslot in which the second voltage $V_{DC2}$ is output. The first switch $SW_1$ is configured and/or controlled to switch on during a first interval in the timeslot and off during a second interval in the timeslot. The fifth switch $SW_5$ is off during the first interval in the timeslot and on during the second interval in the timeslot. An inductor current may decrease during the second interval, and the fifth switch $SW_5$ may be turned off even in the middle of the second interval when the inductor current reaches 0. Although the switching operation of the buck converter is described with reference to FIG. 8 for convenience of description, examples are not limited thereto. For example, a switching operation of the boost converter or the buck-boost converter using the eighth switch $SW_8$ in lieu of the third switch $SW_3$ is also applicable.

FIGS. 9 through 12 are diagrams illustrating examples of a switching operation to output a current.

A desirable DC-AC voltage-current conversion may be desired to generate and output a current through an inductor from a battery. Here, rectification control is desired to constantly fix and regulate an output current, and thus closed-loop control may be applied. The output current may be a stimulating current configured to be applied to a living tissue of a user or a current to be applied to measure an impedance, and have a predefined waveform. An inductor may be used to implement a highly efficient power conversion stimulator or current generator. An accurate magnitude of a current may need to be output at a set time, and thus peak current control and fixed on-time control may be performed.

Figure 9:
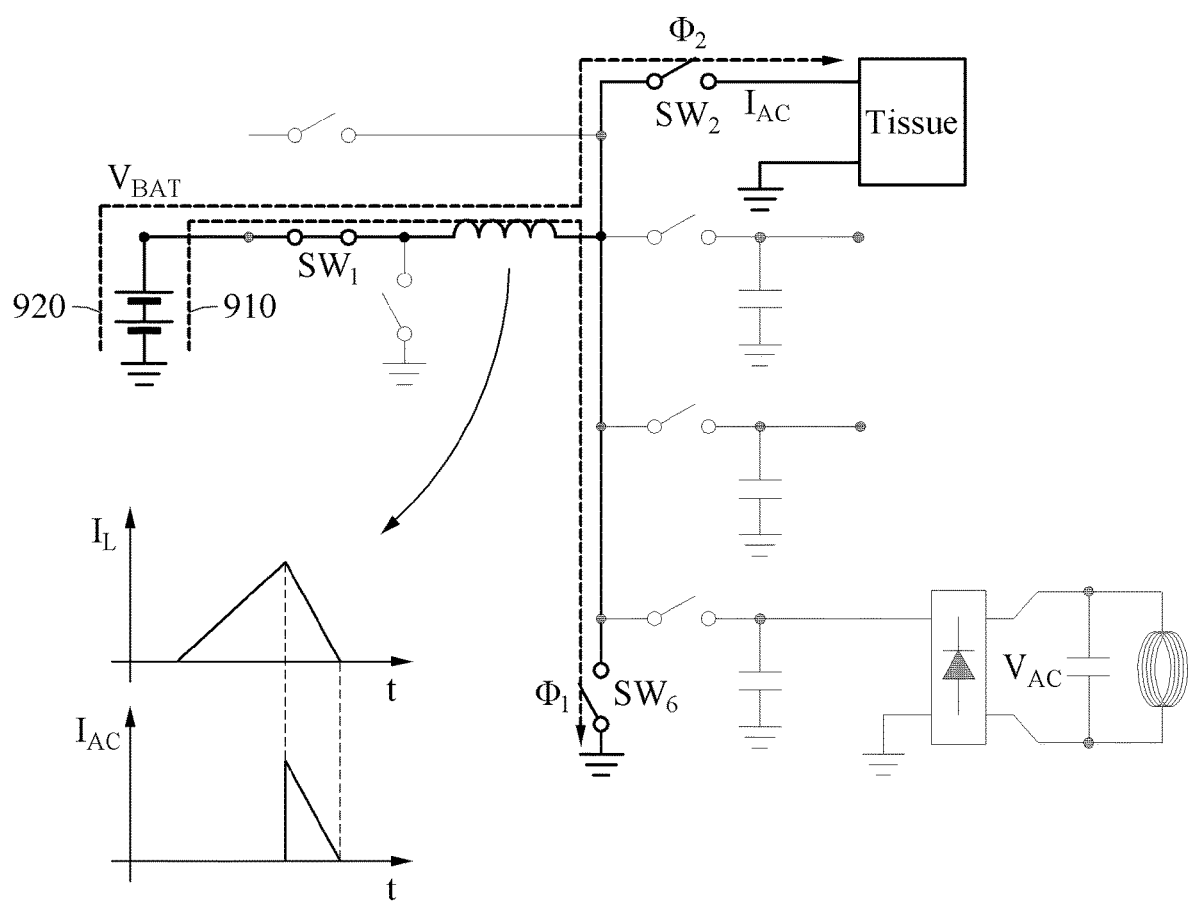
FIGS. 9 through 12 are diagrams illustrating examples of a switching operation to output a current.

FIG. 9 illustrates an example of how a current $I_{AC}$ is output through a switching operation corresponding to operations of a boost converter. The switching operation of the boost converter may be performed when a voltage of a current output end, based on a load on a living tissue to which the current $I_{AC}$ is to be applied, is greater than a battery voltage $V_{BAT}$.

Referring to FIG. 9, the switching operation performed to output the current $I_{AC}$ uses a first switch $SW_1$, a second switch $SW_2$, and a sixth switch $SW_6$. The first switch $SW_1$ is configured and/or controlled to switch on during a timeslot in which the current $I_{AC}$ is output. The sixth switch $SW_6$ is configured and/or controlled to switch on during a first interval in the timeslot and off during a second interval in the timeslot. The second switch $SW_2$ is off during the first interval in the timeslot and on during the second interval in the timeslot. An inductor current may decrease during the second interval, and the second switch $SW_2$ may be turned off when the inductor current reaches 0. That is, a current flow during the first interval in the timeslot in which the current $I_{AC}$ is output is as indicated by a first arrow 910, and a current flow during the second interval in the timeslot in which the current $I_{AC}$ is output is as indicated by a second arrow 920. In this example, an inductor current $I_L$ increases in the first interval and decreases in the second interval, and the inductor current $I_L$ in the second interval is output as the current $I_{AC}$.

Figure 10:
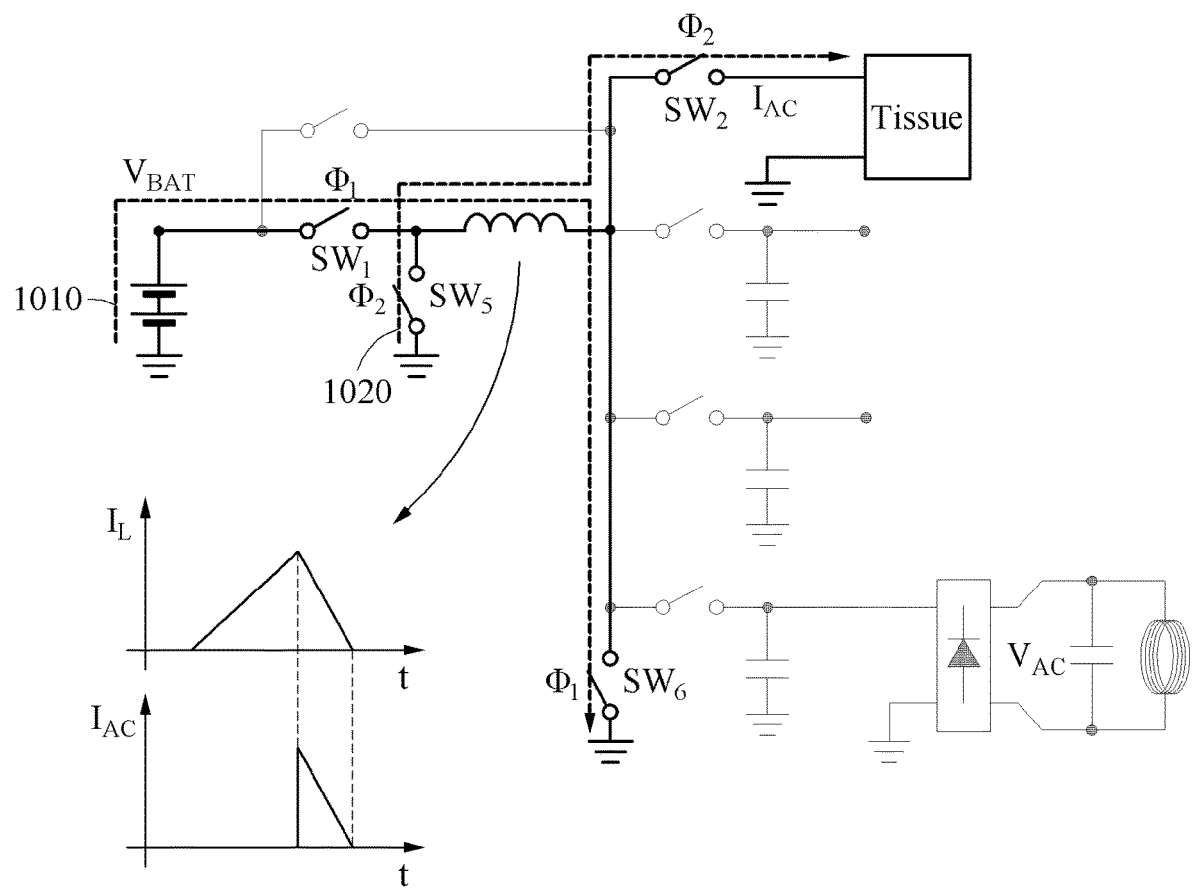

FIG. 10 illustrates an example of how a current $I_{AC}$ is output through a switching operation corresponding to operations of a buck-boost converter. The switching operation of the buck-boost converter may be performed when a voltage of a current output end based on a load on a living tissue to which the current $I_{AC}$ is to be applied is greater than, less than, or equal to a battery voltage $V_{BAT}$.

Referring to FIG. 10, the switching operation performed to output the current $I_{AC}$ uses a first switch $SW_1$, a second switch $SW_2$, a fifth switch $SW_5$, and a sixth switch $SW_6$. The first switch $SW_1$ and the sixth switch $SW_6$ are on during a first interval in a timeslot in which the current $I_{AC}$ is output, and off during a second interval in the timeslot. The second switch $SW_2$ and the fifth switch $SW_5$ are off during the first interval in the timeslot and on during the second interval in the timeslot. An inductor current may decrease during the second interval, and the fifth switch $SW_5$ may be turned off even in the middle of the second interval when the inductor current reaches 0. That is, a current flow during the first interval in the timeslot in which the current $I_{AC}$ is output is as indicated by a first arrow 1010, and a current flow during the second interval in the timeslot in which the current $I_{AC}$ is output is as indicated by a second arrow 1020. In this example, an inductor current $I_L$ increases in the first interval and decreases in the second interval, and the inductor current $I_L$ in the second interval is output as the current $I_{AC}$.

Figure 11:
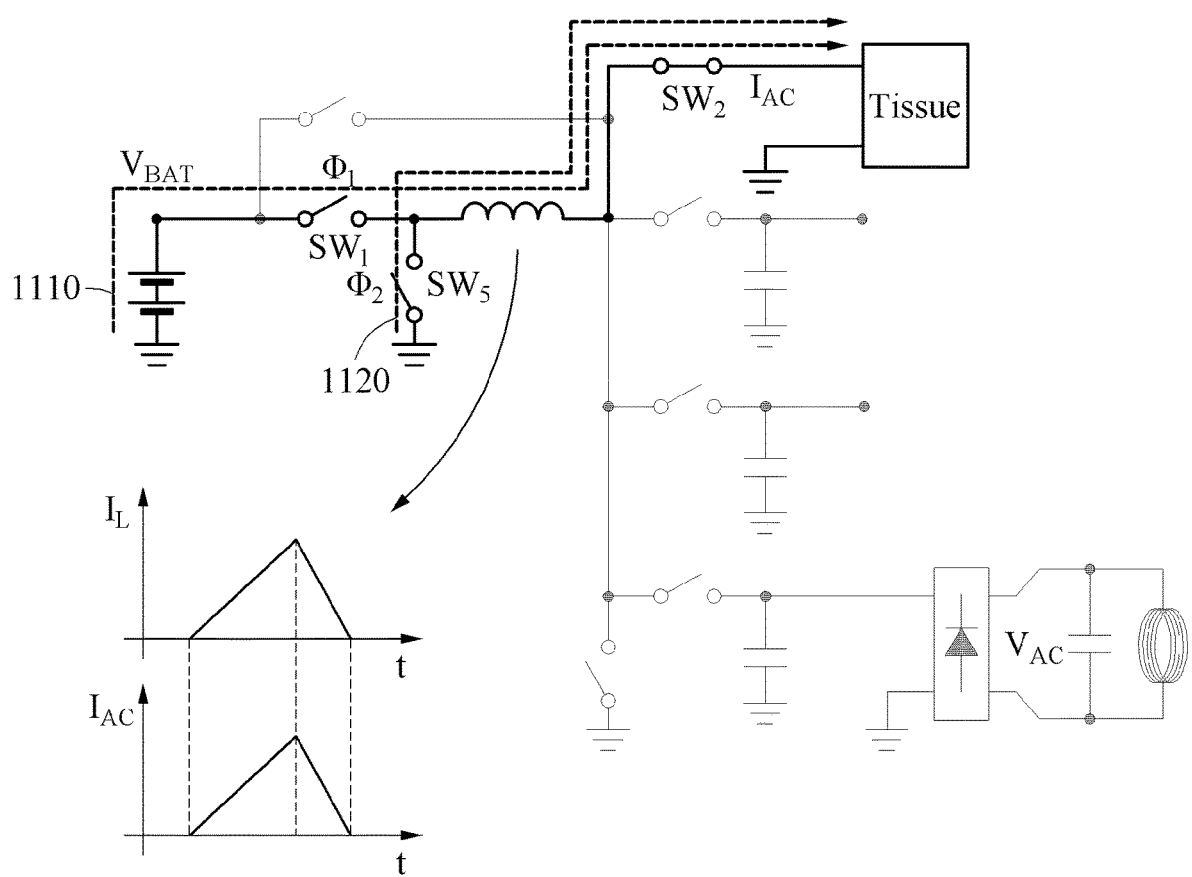

FIG. 11 illustrates an example of how a current $I_{AC}$ is output through a switching operation corresponding to a buck converter. The switching operation of the buck converter may be performed when a voltage of a current output end based on a load on a living tissue to which the current $I_{AC}$ is to be applied is less than a battery voltage $V_{BAT}$.

Referring to FIG. 11, the switching operation performed to output the current $I_{AC}$ uses a first switch $SW_1$, a second switch $SW_2$, and a fifth switch $SW_5$. The second switch $SW_2$ is configured and/or controlled to switch on during a timeslot in which the current $I_{AC}$ is output. The first switch $SW_1$ is configured and/or controlled to switch on during a first interval in the timeslot and off during a second interval in the timeslot. The fifth switch $SW_5$ is off during the first interval in the timeslot and on during the second interval in the timeslot. An inductor current may decrease during the second interval, and the fifth switch $SW_5$ may be turned off even in the middle of the second interval when the inductor current reaches 0. That is, a current flow during the first interval in the timeslot in which the current $I_{AC}$ is output is as indicated by a first arrow 1110, and a current flow during the second interval in the timeslot in which the current $I_{AC}$ is output is as indicated by a second arrow 1120. In this example, an inductor current $I_L$ increases in the first interval and decreases in the second interval, and the inductor current $I_L$ in the first interval and the second interval is output as the current $I_{AC}$.

The examples described above with reference to FIGS. 9 through 11 are related to the current $I_{AC}$ which is a positive current. An example related to a current $I_{AC}$ which is a negative current will be described hereinafter with reference to FIG. 12.

Figure 12:
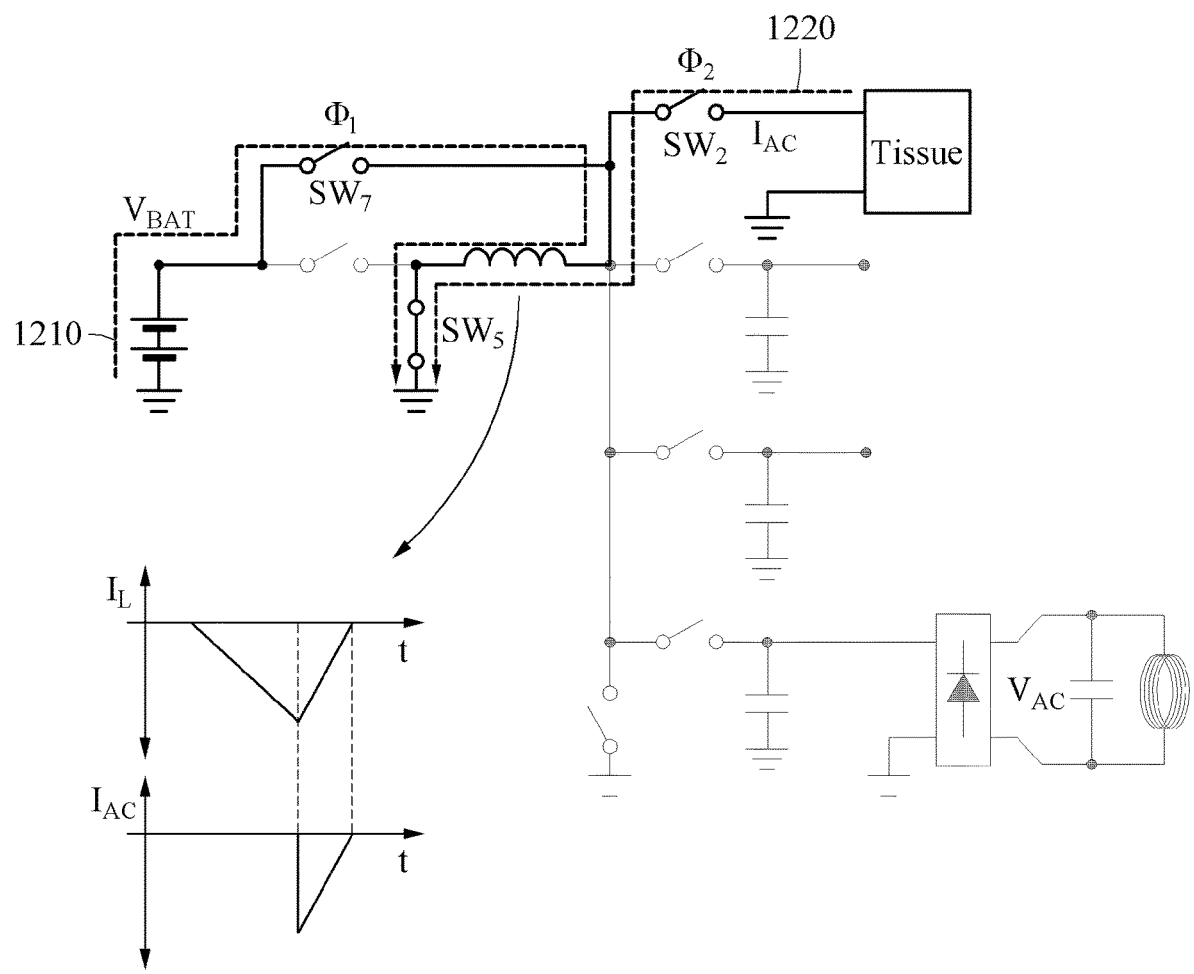

FIG. 12 illustrates an example of how a current $I_{AC}$, a negative current, is output through a switching operation corresponding to operations of a buck-boost converter. The switching operation of the buck-boost converter may be performed when a voltage of a current output end based on a load on a living tissue to which the current $I_{AC}$ is to be applied is greater than, less than, or equal to a battery voltage $V_{BAT}$.

Referring to FIG. 12, the switching operation performed to output the current $I_{AC}$ uses a second switch $SW_2$, a fifth switch $SW_5$, and a seventh switch $SW_7$. The fifth switch $SW_5$ is configured and/or controlled to switch on during a timeslot in which the current $I_{AC}$ is output. The seventh switch $SW_7$ is configured and/or controlled to switch on during a first interval in the timeslot and off during a second interval in the timeslot. The second switch $SW_2$ is off during the first interval in the timeslot and on during the second interval in the timeslot. An inductor current may decrease during the second interval, and the second switch $SW_2$ may be turned off even in the middle of the second interval when the inductor current reaches 0. That is, a current flow during the first interval in the timeslot in which the current $I_{AC}$ is output is as indicated by a first arrow 1210, and a current flow during the second interval in the timeslot in which the current $I_{AC}$ is output is as indicated by a second arrow 1220. In this example, the absolute value of an inductor current $I_L$ increases in the first interval and decreases in the second interval. The inductor current $I_L$ in the second interval is output as the current $I_{AC}$. Thus, both positive and negative currents may be output through the switching operation without an H-bridge connection to the current output end.

FIGS. 13 through 16 are diagrams illustrating examples of controlling switching operations.

The switching operations described above may be performed based on time division-based control. That is, the switching operations may be performed in different timeslots, and use an inductor in their corresponding timeslots. Further, the switching operations may be performed based on time division-based priority control. For example, one switching operation selected from the switching operations based on their priorities may be performed in a current timeslot. The time division-based priority control will be described in detail with reference to FIG. 13.

Figure 13:
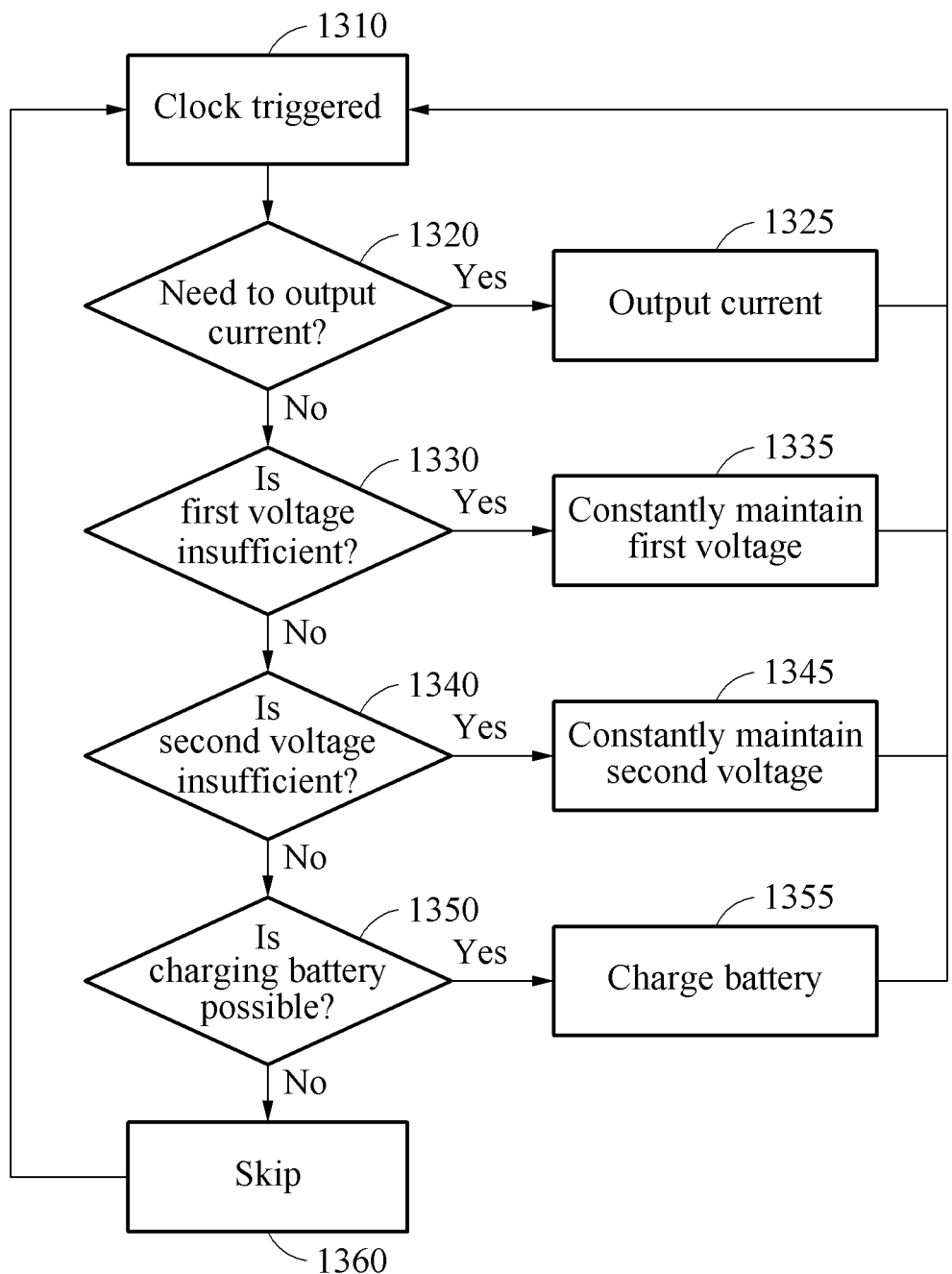
FIGS. 13 through 16 are diagrams illustrating examples of controlling switching operations.

FIG. 13 illustrates a flowchart of a switching operation controlled based on the time division-based priority control.

Referring to FIG. 13, in operation 1310, a new timeslot is allocated through a clock trigger. When the new timeslot is allocated, operation 1320 is performed.

In operation 1320, whether a current needs to be output from a current output end is determined. For example, whether a stimulating current needs to be output to a living tissue being in contact with the current output end may be determined. For another example, whether a current needs to be output to measure an impedance on a portion being in contact with the current output end may be determined. In response to a determination that it needs to output a current, operation 1325 is performed. In response to a determination that it does not need to output a current, operation 1330 is performed.

In operation 1325, a switching operation to output a current is performed during the current timeslot, and a current is output from the current output end. Operation 1310 is then performed, and a next timeslot ensues.

In operation 1330, whether a first voltage output from a first voltage output end is insufficient is determined. Such determination may be performed based on whether a current voltage of the first voltage output end is less than a preset first reference voltage. For example, when the first reference voltage is 1.80V, and the current voltage of the first voltage output end is 1.85V or 1.80V, it may be determined that the first voltage is not insufficient. In this example, when the current voltage of the first voltage output end is 1.75V, it may be determined that the first voltage is insufficient. In response to a determination that the first voltage is insufficient, operation 1335 is then performed. In response to a determination that the first voltage is not insufficient, operation 1340 is then performed.

In operation 1335, a switching operation to constantly maintain the first voltage output from the first voltage output end to be the first reference voltage is performed during the current timeslot. That is, energy may be transferred to the first voltage output end, and thus the first voltage may be maintained at the first reference voltage. Operation 1310 is then performed, and a next timeslot ensues.

In operation 1340, whether a second voltage output from a second voltage output end is insufficient is determined. Such determination may be performed based on whether a current voltage of the second voltage output end is less than a preset second reference voltage. For example, when the second reference voltage is 0.80V, and the current voltage of the second voltage output end is 0.85V or 0.80V, it may be determined that the second voltage is not insufficient. In this example, when the current voltage of the second voltage output end is 0.75V, it may be determined that the second voltage is insufficient. In response to a determination that the second voltage is insufficient, operation 1345 is then performed. In response to a determination that the second voltage is not insufficient, operation 1350 is then performed.

In operation 1345, a switching operation to constantly maintain the second voltage output from the second voltage output end to be the second reference voltage is performed during the current timeslot. That is, energy may be transferred to the second voltage output end. Operation 1310 is then performed, and a next timeslot ensues.

In operation 1350, whether charging a battery is possible is determined. Such determination may be performed based on whether a rectifier voltage suffices. For example, when a reference rectifier voltage is 1.0V, and the rectifier voltage is 1.0V or 1.1V, it may be determined that charging the battery is possible. In this example, when the rectifier voltage is 0.9V, it may be determined that charging the battery is not possible. In response to a determination that charging the battery is possible, operation 1355 is then performed. In response to a determination that charging the battery is not possible, operation 1360 is then performed.

In operation 1355, a switching operation to charge the battery is performed during the current timeslot, and the battery is then charged. Operation 1310 is then performed, and a next timeslot ensues.

In operation 1360, the current timeslot is skipped when it is determined that there is no need to output a current, maintain a voltage, and charge the battery, or it is not possible to output a current, maintain a voltage, and charge the battery. That is, any switching operations are not performed in the current timeslot, and operation 1310 is then performed and a next timeslot ensues.

As described above, the time division-based priority control may be performed by dividing a time axis and performing a high-priority switching operation first. For example, a point in time at which stimulation is applied may be of importance when a stimulating signal is applied, and thus a switching operation to output a current may have the highest priority. However, when charging the battery, a point in time may be of less importance and only transferring power to the battery suffices, and thus a switching operation for charging the battery may have the lowest priority. In addition, when maintaining a voltage, a point in time at which a voltage is maintained may be of less important, and a voltage of a voltage output end needs to be maintained to be greater than or equal to a preset reference voltage, and thus a switching operation to maintain a voltage may have a medium priority.

Figure 14:
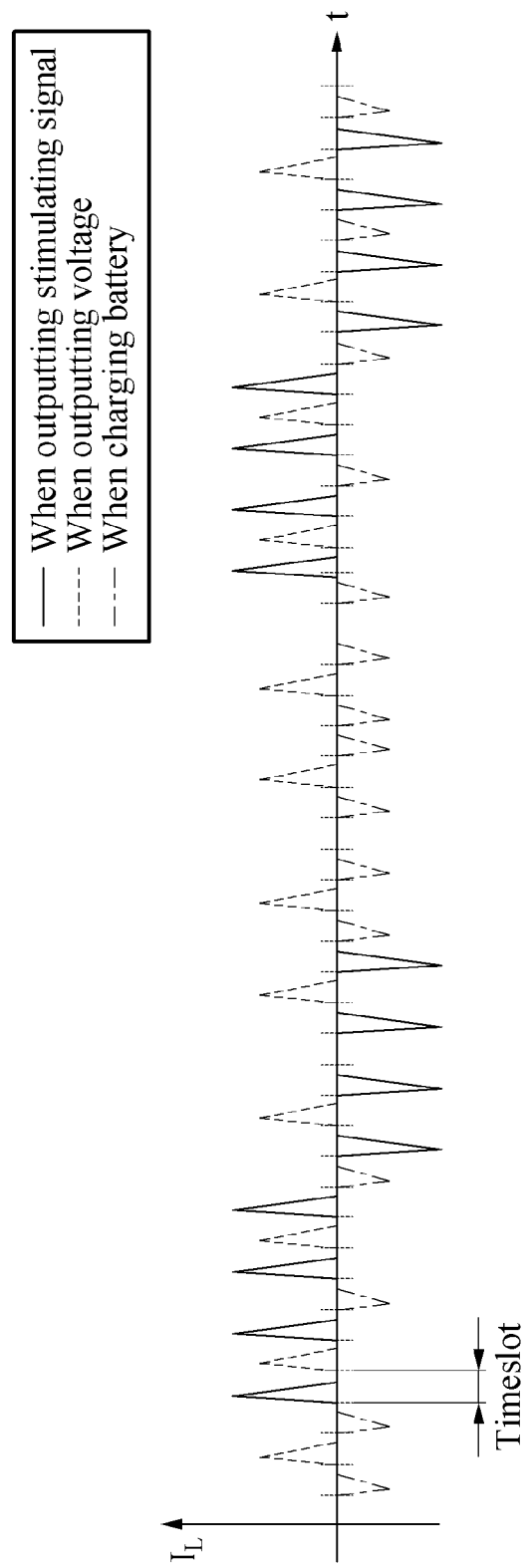

FIG. 14 illustrates an example of an inductor current $I_L$ when a switching operation is performed based on time division-based priority control. Referring to FIG. 14, a switching operation to output a current, maintain a voltage, or charge a battery may be performed in one timeslot. For example, when outputting a current for stimulation, a pattern in which a preset number of currents is output in a positive direction and then a preset number of currents is output in a negative direction may be shown. In this example, a certain blank period may be present between such patterns. In a timeslot that is not allocated to output a current, a voltage may be output. In a timeslot that is not allocated to maintain a voltage in addition to the outputting of a current, the battery may be charged. In addition, a timeslot that is not allocated for charging the battery in addition to the outputting of a current and the maintaining of a voltage may be skipped, and thus an inductor current $I_L$ may not flow in this timeslot.

A direction of an inductor current $I_L$ when charging the battery is opposite to a direction of an inductor current $I_L$ when outputting a positive current or when maintaining a voltage, and thus the inductor current $I_L$ may have a negative value as shown in a graph illustrated in FIG. 14.

In an example, the speed of a reference clock used to divide timeslots may be controllable. For example, when, although charging the battery is frequently required, the charging of the battery is not sufficiently performed due to the outputting of a current or the maintaining of a voltage, the clock speed may be controlled to be faster. However, when a timeslot is generated more frequently than the requirement for the outputting of a current, the maintaining of a voltage, or the charging of the battery, a pulse-skip rate may increase. When the pulse-skip rate increases, the clock speed may be controlled to be slower. By adaptively controlling the clock speed as described above, a more stable switching operation may be performed.

Figure 15:
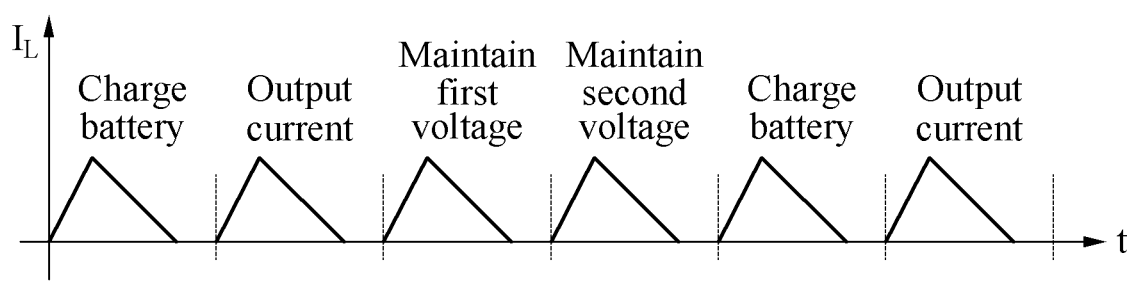

FIG. 15 illustrates an example of time division-based sequential control. In an example, switching operations may be allocated in sequential order to timeslots. For example, switching operations to charge a battery, output a current, maintain the first voltage, and maintain a second voltage, respectively, may be sequentially allocated to the timeslots and then be performed. Through the time division-based sequential control, an operation of determining a switching operation in a timeslot may be omitted.

Figure 16:
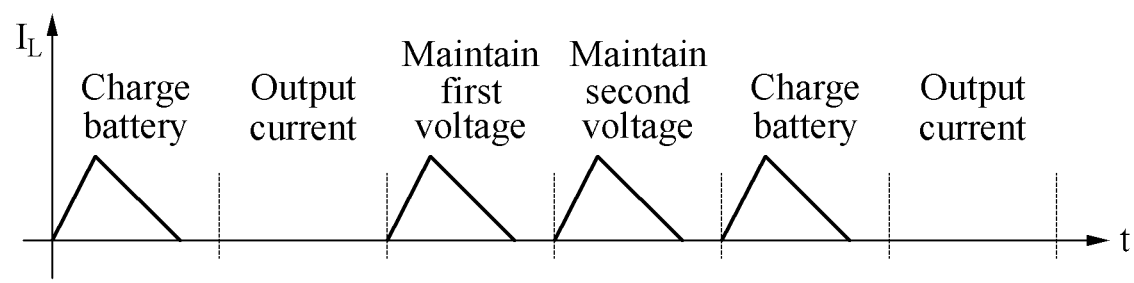

FIG. 16 illustrates an example without a need to output a current in the process of time division-based sequential control. For example, when there is no need to output a current in a current timeslot in the time division-based sequential control, the timeslot may be skipped irrespective of whether there is a need to maintain a voltage or whether charging a battery is possible.

In FIGS. 15 and 16, even though the switching operations are allocated in sequential order to different timeslots as an example, the depicted orders are not limited thereto in other examples. For example, examples include the switching operations being allocated in an order that may include any one or any combination of any two or more of the switching operations to charge the battery, output the current, maintain the first voltage, and maintain the second voltage.

Figure 17:
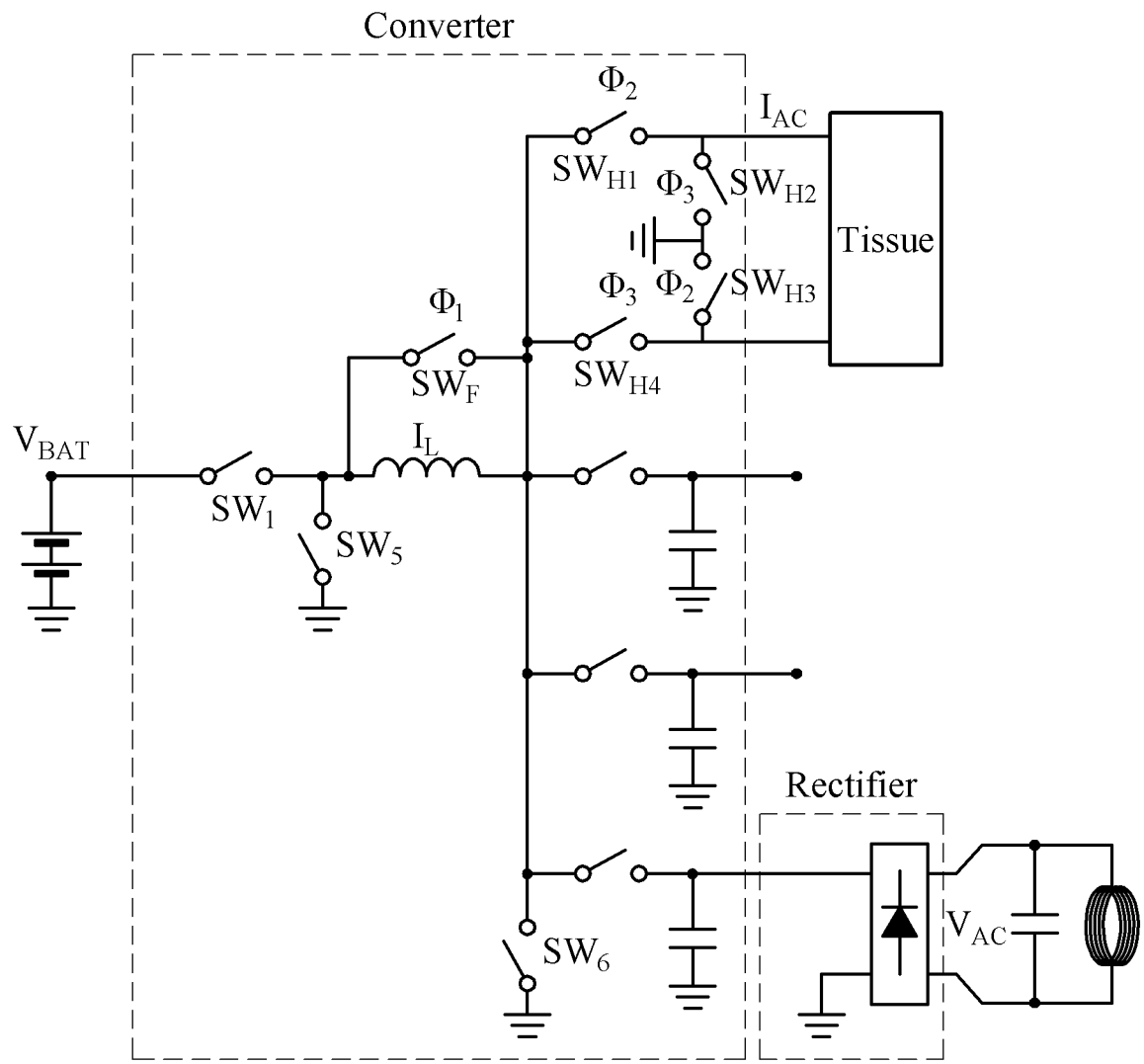

FIGS. 17 and 18 are diagrams illustrating examples of a switching operation to output a pulsed current using a freewheeling switch.

In an example, a current to be output from a current output end may be output not in a form of triangular or chopping wave, but in the form of a pulse wave. Thus, an inductance, or a value of an inductor included in a converter, may need to be sufficiently large such that a waveform of the inductor does not drop due to a voltage at both ends of a living tissue. The converter may further include a freewheeling switch $SW_F$, and the second switch $SW_2$ described above may be embodied as an H-bridge. Hereinafter, a switching operation performed to output a current in a form of pulse wave will be described in detail with reference to FIGS. 17 and 18.

FIG. 17 is a circuit diagram illustrating an example of a switching operation to output a current in a form of pulse wave. Referring to FIG. 17, a first switch $SW_1$ and a sixth switch $SW_6$ are on to build up a current into an inductor current $I_L$. In addition, the first switch $SW_1$ and the sixth switch $SW_6$ are off and the freewheeling switch $SW_F$ is configured and/or controlled to switch on to maintain the inductor current $I_L$ to be constant. In a closed loop including the inductor and the freewheeling switch $SW_F$, the inductor current $I_L$ may flow counterclockwise.

Then, when the freewheeling switch $SW_F$ is off, and some switches of the H-bridge, for example, $SW_{H1}$ and $SW_{H3}$, and the fifth switch $SW_5$ or the first switch $SW_1$ are on, a current $I_{AC}$ may be output in a positive direction. Conversely, when the freewheeling switch $SW_F$ is off and remaining switches of the H-bridge, for example, $SW_{H2}$ and $SW_{H4}$ and the fifth switch $SW_5$ or the first switch $SW_1$ are on, the current $I_{AC}$ may be output in a negative direction.

In an example, one pulse may be output in one timeslot. To output a current in the form of the positive pulse wave, the freewheeling switch $SW_F$ may be on during a first interval in the timeslot and off during a second interval in the timeslot. In addition, the switches $SW_{H1}$ and $SW_{H3}$ of the H-bridge, and the fifth switch $SW_5$ or the first switch $SW_1$ may be off during the first interval in the timeslot and on during the second interval in the timeslot. Conversely, to output a current in the form of the negative pulse wave, the freewheeling switch $SW_F$ may be on during the first interval in the timeslot and off during the second interval in the timeslot. In addition, the remaining switches $SW_{H2}$ and $SW_{H4}$ of the H-bridge, and the fifth switch $SW_5$ or the first switch $SW_1$ may be off during the first interval in the timeslot and on during the second interval in the timeslot. In this example, based on such control on the first switch $SW_1$, the fifth switch $SW_5$, the sixth switch $SW_6$, and the freewheeling switch $SW_F$, it may be assumed that a switching operation to constantly maintain the inductor current $I_L$ is already performed.

FIG. 18 illustrates respective examples of an inductor current $I_L$, a current $I_{AC}$ to be output, a first control voltage $\phi_1$, a second control voltage $\phi_2$, and a third control voltage $\phi_3$. Referring to FIG. 18, when the first control voltage $\phi_1$ is in its high, a switch to be controlled by the first control voltage $\phi_1$ is configured and/or controlled to switch on. Conversely, when the first control voltage $\phi_1$ is in its low, the switch to be controlled by the first control voltage $\phi_1$ is off. Likewise, whether switches corresponding to the second control voltage $\phi_2$ and the third control voltage $\phi_3$ are on or off may also be controlled.

The inductor current $I_L$ that is constantly maintained as illustrated in FIG. 18 may be output as the current $I_{AC}$ in the form of positive pulse wave under the control of the first control voltage $\phi_1$ and the second control voltage $\phi_2$. In addition, the inductor current $I_L$ may be output as the current $I_{AC}$ in the form of negative pulse wave under the control of the first control voltage $\phi_1$ and the third control voltage $\phi_3$.

As described above, by embodying freewheeling by short-circuiting both ends of an inductor by a freewheeling switch $SW_F$, it is possible to maintain an inductor current $I_L$ to be a DC. In addition, control on the freewheeling switch $SW_F$ and an H-bridge may allow a current $I_{AC}$ in the form of pulse wave to be output.

The circuit device 100, the converter 110, the power receiver 120, the battery 130, the controller 140, the inductor 111, the switching circuit 113, the switches, converter, the circuit device, and other apparatuses, modules, devices, and other components described herein with respect to FIGS. 1-18 are implemented by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples, multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-18 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A converter device, comprising:
an inductor having a first end and a second end; and
a switching circuit, connected to the inductor, comprising:
a first switch configured to control a connection between the first end of the inductor and a battery connected to the converter device;
an H-bridge comprising a plurality of switches including a second switch, the H-bridge configured to control a connection between the second end of the inductor and a current output end configured to output a current generated through the inductor from the battery;
a third switch configured to control a connection between the second end of the inductor and a voltage output end configured to output a voltage generated from the battery;
a fourth switch configured to control a connection between the second end of the inductor and a voltage input end configured to receive a voltage to charge the battery; and a freewheeling switch configured to control a connection between the first end of the inductor and the second end of the inductor;
wherein the H-bridge is connected to the second end of the inductor and configured to control a direction in which the current is provided by the current output end,
wherein the freewheeling switch is on during a first interval in a timeslot in which the current is provided and off during a second interval in the timeslot,
wherein a portion of switches of the H-bridge and a fifth switch are off during the first interval in the timeslot and on during the second interval in the timeslot, and
wherein the current is in a form of a pulse wave.

2. A circuit device, comprising:
a battery;
a power receiver configured to receive power to charge the battery;
a converter connected to the battery and the power receiver, comprising an inductor and a switching circuit; and a controller configured to control switching operations of the switch circuit to provide a switch-on connection of the battery to a first side of the inductor and perform:
  a first switching operation to charge the battery by a voltage at a second side of the inductor generated from an input voltage to the converter; and
  at least one of:
  a second switching operation to generate a current source, at an output of the converter, from the second side of the inductor, or
  a third switching operation to generate a maintained constant voltage, at another output of the converter, from another voltage at the second side of the inductor;
wherein the switching circuit further comprises:
  a freewheeling switch configured to control a connection between a first end of the inductor and a second end of the inductor, and
  an H-bridge comprising a plurality of switches including a second switch, wherein the H-bridge is connected to the second end of the inductor and configured to control a direction in which a current is provided by the current source;
wherein the freewheeling switch is on during a first interval in a timeslot in which the current source is provided and off during a second interval in the timeslot, and
wherein a portion of switches of the H-bridge and a fifth switch are off during the first interval in the timeslot and on during the second interval in the timeslot, and
wherein the current is in a form of a pulse wave.

3. The circuit device of claim 2, wherein the controller is configured to cause at least two of the first switching operation to be performed during a first timeslot, the second switching operation to be performed during a separate second timeslot, or the third switching operation to be performed during a separate third timeslot.

4. A converter device, comprising:
  an inductor having a first end and a second end; and
  a switching circuit, connected to the inductor, comprising:
    a first switch configured to generate a connection between the first end of the inductor and a battery;
    an H-bridge comprising a plurality of switches including a second switch, the H-bridge configured to generate a connection between the second end of the inductor and a current output end that provides a current source generated through the inductor from the battery;
    a third switch configured to generate a connection between the second end of the inductor and a voltage output end that outputs a first voltage generated through the inductor from the battery;
    a fourth switch configured to generate a connection between the second end of the inductor and a voltage input end that receives a second voltage that charges the battery with the first switch generated connection; and
    a freewheeling switch configured to control a connection between the first end of the inductor and the second end of the inductor;
  wherein the H bridge is connected to the second end of the inductor and configured to control a direction in which a current is provided by the current source,
  the freewheeling switch is on during a first interval in a timeslot in which the current source is provided and off during a second interval in the timeslot,
  a portion of switches of the H-bridge and a fifth switch are off during the first interval in the timeslot and on during the second interval in the timeslot, and
  wherein the current is in a form of a pulse wave.

5. The converter device of claim 4, wherein the switching circuit further comprises:
  a fifth switch configured to control a connection between the first end of the inductor and a ground;
  a sixth switch configured to control a connection between the second end of the inductor and the ground; and
  a seventh switch configured to control a connection between the second end of the inductor and the battery.

6. The converter device of claim 4, wherein the switching circuit further comprises:
  a sixth switch configured to control a connection between the second end of the inductor and a ground,
  wherein the first switch is on during a timeslot in which the current source is provided,
  the sixth switch is on during a first interval in the timeslot and off during a second interval in the timeslot, and
  the second switch is off during the first interval in the timeslot and on during the second interval in the timeslot.

7. The converter device of claim 4, wherein the switching circuit further comprises:
  a fifth switch configured to control a connection between the first end of the inductor and a ground,
  wherein the second switch is on during a timeslot in which the current source is provided,
  the first switch is on during a first interval in the timeslot and off during a second interval in the timeslot, and
  the fifth switch is off during the first interval in the timeslot and on during the second interval in the timeslot.

8. The converter device of claim 4, wherein the switching circuit further comprises:
  a fifth switch configured to control a connection between the first end of the inductor and a ground; and
  a sixth switch configured to control a connection between the second end of the inductor and the ground,
  wherein the first switch and the sixth switch are on during a first interval in a timeslot in which the current source is provided and off during a second interval in the timeslot, and
  the second switch and the fifth switch are off during the first interval in the timeslot and on during the second interval in the timeslot.

9. The converter device of claim 4, wherein the switching circuit further comprises:
  a fifth switch configured to control a connection between the first end of the inductor and a ground; and
  a seventh switch configured to control a connection between the second end of the inductor and the battery,
  wherein the fifth switch is on during a timeslot in which the current source is provided,
  the seventh switch is on during a first interval in the timeslot and off during a second interval in the timeslot, and
  the second switch is off during the first interval in the timeslot and on during the second interval in the timeslot.

10. The converter device of claim 4, wherein the switching circuit is configured to perform a switching operation on internal switches such that a first current is provided by the current source during a first timeslot and a second current is provided, in a direction opposite to a direction of the first current, by the current source during a second timeslot different from the first timeslot.

11. The converter device of claim 4, wherein the switching circuit further comprises:
   a sixth switch configured to control a connection between the second end of the inductor and a ground,
   wherein the first switch is on during a timeslot in which the first voltage is output,
   the sixth switch is on during a first interval in the timeslot and off during a second interval in the timeslot, and
   the third switch is off during the first interval in the timeslot and on during the second interval in the timeslot.

12. The converter device of claim 4, wherein the switching circuit further comprises:
   a fifth switch configured to control a connection between the first end of the inductor and a ground,
   wherein the third switch is on during a timeslot in which the first voltage is output,
   the first switch is on during a first interval in the timeslot and off during a second interval in the timeslot, and
   the fifth switch is off during the first interval in the timeslot and on during the second interval in the timeslot.

13. The converter device of claim 4, wherein the switching circuit further comprises:
   a fifth switch configured to control a connection between the first end of the inductor and a ground; and
   a sixth switch configured to control a connection between the second end of the inductor and the ground,
   wherein the first switch and the sixth switch are on during a first interval in a timeslot in which the first voltage is output and off during a second interval in the timeslot, and
   the third switch and the fifth switch are off during the first interval in the timeslot and on during the second interval in the timeslot.

14. The converter device of claim 4, wherein the switching circuit further comprises:
   a fifth switch configured to control a connection between the first end of the inductor and a ground,
   wherein the fourth switch is on during a timeslot in which the battery is charged,
   the fifth switch is on during a first interval in the timeslot and off during a second interval in the timeslot, and
   the first switch is off during the first interval in the timeslot and on during the second interval in the timeslot.

15. The converter device of claim 4, wherein the switching circuit is configured to perform at least two of a first switching operation to output the current generated through the inductor during a first timeslot, a second switching operation to maintain the first voltage to be constant during a second timeslot, or a third switching operation to charge the battery during a third timeslot.

16. The converter device of claim 4, wherein the switching circuit is configured to perform at least one of a first switching operation to provide the current source during a first timeslot, a second switching operation to maintain the first voltage to be constant during a second timeslot, or a third switching operation to charge the battery during a third timeslot, and
   wherein the switching circuit is configured to perform one switching operation selected from the first switching operation, the second switching operation, and the third switching operation, based on priorities of the first switching operation, the second switching operation, and the third switching operation.

17. The converter device of claim 16, wherein, upon a determination to provide the current source, the switching circuit performs the first switching operation.

18. The converter device of claim 16, wherein, upon a determination not to provide the current source and the first voltage is determined insufficient, the switching circuit is configured to perform the second switching operation.

19. The converter device of claim 16, wherein, upon a determination that a charging of the battery is possible, a determination not to provide the current source, and the first voltage being determined sufficient, the switching circuit performs the third switching operation.

20. The converter device of claim 16, wherein, upon a determination not to provide the current source and the first voltage being determined sufficient, and a determination that a charging of the battery is not possible, the switching circuit skips a respective one of the first timeslot, the second timeslot, and the third timeslot.

21. The converter device of claim 4, wherein the portion of switches of the H-bridge is selected from switches included in the H-bridge based on a direction in which the current of the current source is provided.

22. The converter device of claim 4, wherein the inductor is a single inductor.

23. The converter device of claim 4, wherein the switching circuit further comprises:
   an eighth switch configured to control a connection between the second end of the inductor and a second voltage output end to another voltage generated through the inductor from the battery is output.

24. The converter device of claim 4, configured to be implanted in a human body.

25. The converter device of claim 4, wherein the first voltage is a constant voltage provided to one of a controller and a sensor that are connected to the converter.

26. The converter device of claim 4, wherein the converter device is a circuit device and further comprises a battery, a power receiver configured to receive power to charge the battery, and wherein a controller is configured to control switching operations of the switching circuit.

27. The converter device of claim 4, wherein the switching circuit is configured to perform at least two of a first switching operation to output the current generated through the inductor from the battery during a first timeslot, a second switching operation to maintain the first voltage to be constant during a separate second timeslot, or a third switching operation to charge the battery during a separate third timeslot.

* * * * *